United States Patent
Nicolson et al.

(10) Patent No.: US 11,322,262 B2
(45) Date of Patent: May 3, 2022

(54) SYSTEM AND METHOD FOR CONSULTING ON CULTURE PLATE READINGS

(71) Applicant: Becton, Dickinson and Company, Franklin Lakes, NJ (US)

(72) Inventors: Strett Roger Nicolson, Owings Mills, MD (US); Rajeev Sehgal, Cockeysville, MD (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 234 days.

(21) Appl. No.: 16/348,843

(22) PCT Filed: Nov. 9, 2017

(86) PCT No.: PCT/US2017/060930
§ 371 (c)(1),
(2) Date: May 9, 2019

(87) PCT Pub. No.: WO2018/089683
PCT Pub. Date: May 17, 2018

(65) Prior Publication Data
US 2020/0185113 A1    Jun. 11, 2020

Related U.S. Application Data

(60) Provisional application No. 62/420,470, filed on Nov. 10, 2016.

(51) Int. Cl.
*H04L 29/06* (2006.01)
*H04N 7/15* (2006.01)
(Continued)

(52) U.S. Cl.
CPC ......... *G16H 80/00* (2018.01); *G06F 3/04847* (2013.01); *G10L 25/51* (2013.01);
(Continued)

(58) Field of Classification Search
CPC ............... H04N 7/185; H04N 1/00307; H04N 2201/0084; H04N 19/00; G06K 9/0014;
(Continued)

(56) References Cited

U.S. PATENT DOCUMENTS

2003/0147099 A1    8/2003  Heimendinger
2011/0126127 A1*   5/2011  Mariotti .............. H04M 7/0027
                                                        715/753
(Continued)

FOREIGN PATENT DOCUMENTS

WO    WO 2013/147610 A1    10/2013
WO    WO 2015/169499 A1    11/2015
(Continued)

OTHER PUBLICATIONS

International Search Report and Written Opinion dated Jan. 22, 2018 for PCT/US2017/060930, filed Nov. 9, 2017.

*Primary Examiner* — Maroun P Kanaan
(74) *Attorney, Agent, or Firm* — Knobbe, Martens, Olson & Bear, LLP

(57) ABSTRACT

Systems and methods are provided for selecting colony locations. Selecting colony locations can include determine a location of a selection tool on a culture plate image, determining a location of a potential source of error on the culture plate image, comparing the location of the selection tool to the location of the potential source of error; and determining an error when the location of the selection tool overlays the location of the potential source of error.

19 Claims, 26 Drawing Sheets

(51) Int. Cl.
*G16H 80/00* (2018.01)
*G16H 40/67* (2018.01)
*G16H 10/40* (2018.01)
*G16H 30/20* (2018.01)
*G16H 30/40* (2018.01)
*G06F 3/04847* (2022.01)
*G10L 25/51* (2013.01)
*H04L 67/104* (2022.01)

(52) U.S. Cl.
CPC ............. *G16H 10/40* (2018.01); *G16H 30/20* (2018.01); *G16H 30/40* (2018.01); *G16H 40/67* (2018.01); *H04L 67/104* (2013.01)

(58) Field of Classification Search
CPC ............. G06K 9/00147; G06K 9/6227; G06K 9/6256; G06K 9/6277; G06K 9/00134; G06K 9/00664; G06K 9/6215; G06K 9/6267; G06K 9/00; H04L 67/02; H04L 43/045; H04L 65/4069; H04L 67/104; H04L 67/12; G06T 9/00; G06T 11/206; G06T 11/60; G06T 2207/10016; G06T 7/20; G06T 2207/30004; G06T 2200/24; G16H 80/00; G16H 10/40; G16H 30/20; G16H 30/40; G16H 40/67; G06F 3/04847; G10L 25/51
See application file for complete search history.

(56) References Cited

U.S. PATENT DOCUMENTS

| | | |
|---|---|---|
| 2014/0227774 A1 | 8/2014 | Guthrie |
| 2015/0086971 A1 | 3/2015 | Botma |
| 2015/0213614 A1* | 7/2015 | Maddah ............. G06T 7/246 |
| | | 382/133 |
| 2016/0145562 A1 | 5/2016 | Pedersen |
| 2016/0210411 A1 | 7/2016 | Mentis |

FOREIGN PATENT DOCUMENTS

| | | |
|---|---|---|
| WO | WO 2016/172388 A2 | 10/2016 |
| WO | WO 2016/191646 A2 | 12/2016 |

* cited by examiner

Initiating User

Consultant User

Initiating User

Consultant User

SYSTEM AND METHOD FOR CONSULTING ON CULTURE PLATE READINGS

RELATED U.S. APPLICATIONS

This application claims priority to U.S. Provisional Appl. No. 62/420,470 filed on Nov. 10, 2016, which is hereby incorporated by reference in its entirety.

BACKGROUND

Field

This invention relates to a consultation system and method for reading biological information, such as growth of colonies on culture plates.

Description of the Related Art

Methods and systems for reading culture plates by a variety of techniques are known. For example, methods for identifying microorganisms using mass spectrometry, in particular MALDI-TOF-MS (Matrix Assisted Laser Desorption and Ionization Time-of-Flight Mass Spectrometry) and the related systems for performing such methods are known. Such systems and methods are described, for example, in WO2013/147610 to Botma et al., the disclosure of which is incorporated by reference herein. Botma et al., teaches a method for locating and selecting a colony of microorganisms by obtaining an initial image of a culture dish, having a researcher or analyst manually select a colony of microorganisms in the initial image. The system then captures a second image of the culture dish from a position below a device for picking up a microorganism sample from the culture dish. The initial image and the second image are then compared to determine which colony was selected.

SUMMARY

Aspects of the invention include systems, devices, and methods for consulting on the analysis of culture plate results.

One embodiment is a system for sharing data related to a culture plate image. The system includes a first device having a user interface configured to display one or more culture plate images and one or more culture plate image annotation tools, an input configured to allow a technician to interact with the user interface, wherein the input is configured to allow manipulation of the one or more annotation tools to annotate the one or more culture plate images, a communications module configured to transmit data to and receive data from one or more external devices or networks, and a processor. The processor is configured to process data received from the user interface, associate one or more annotations performed using the one or more annotation tools with the one or more culture plate images, and instruct the communications module to transmit the one or more culture plate images and one or more annotations associated with the one or more culture plate images to a second device or a computer network.

Another embodiment is a method for sharing data related to a culture plate image. The method includes displaying one or more culture plate images and one or more culture plate image annotation tools on a user interface of a first device, annotating the one or more culture plate images with one or more annotations in response to manipulation of an input, associating each of the one or more annotations with the one or more culture plate images by a processor, and transmitting the one or more culture plate images and one or more annotations associated with the one or more culture plate images to a second device or a computer network by a communications module.

DETAILED DESCRIPTION

Figure 1:
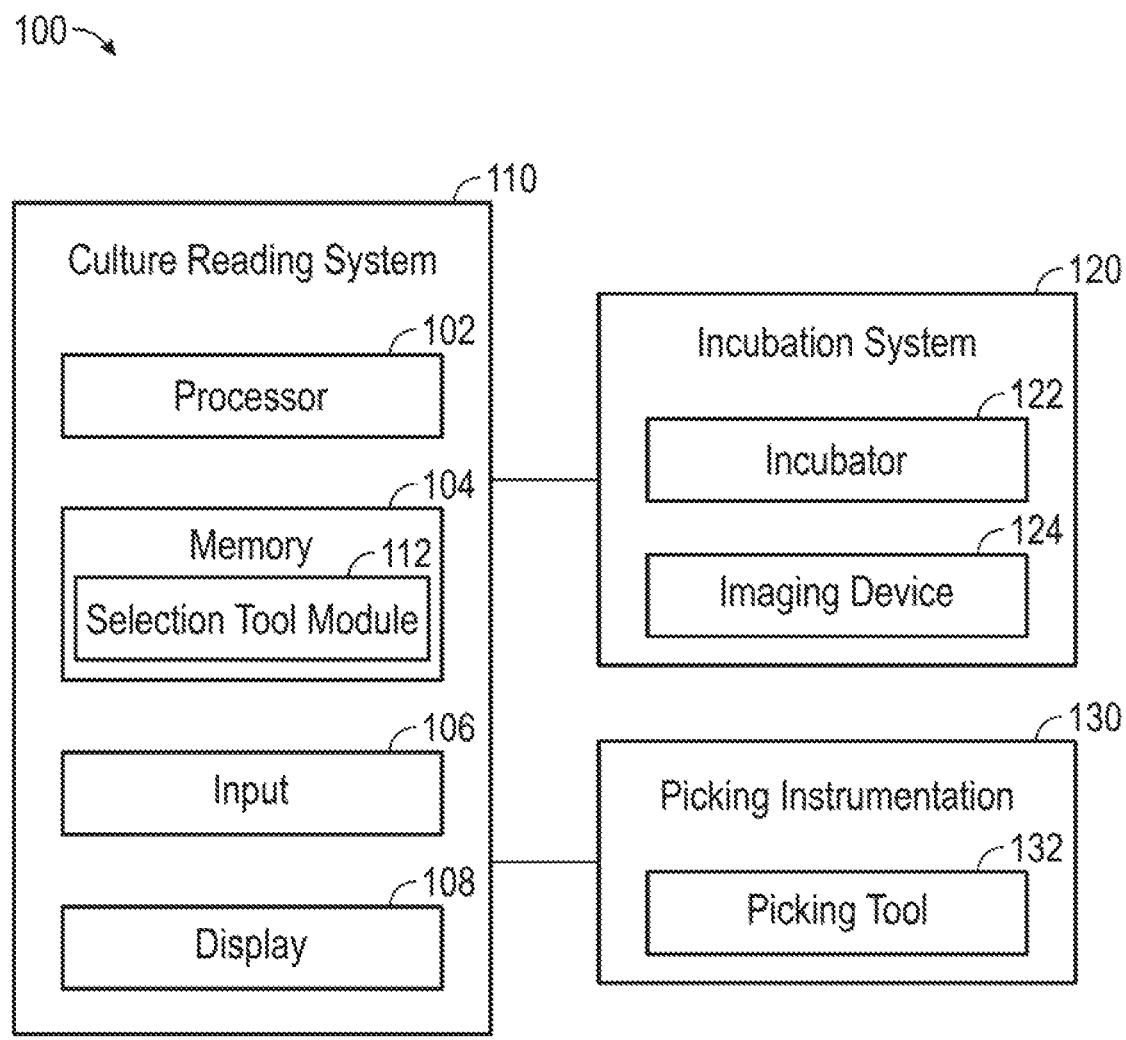
FIG. 1 depicts a schematic view of a colony selection system in accordance with an illustrative embodiment of the present invention.

As will be appreciated by one skilled in the art, there are numerous ways of carrying out the examples, improvements, and arrangements for colony selection in accordance with embodiments of the invention disclosed herein. Although reference will be made to the illustrative embodiments depicted in the drawings and the following description, these embodiments are not meant to be exhaustive of the various alternative designs and embodiments that are encompassed by the disclosed invention. Those skilled in the art will readily appreciate that various modifications may be made, and various combinations can be made, without departing from the invention.

One embodiment is a system for analyzing a culture plate by creating an on-line collaboration or consultation between a user reviewing the culture plate and a remote collaborator or consultant. In this embodiment, the user may pull up a first set of culture plate images to analyze. If the user wants assistance in performing an analysis, the user can select to start a collaboration session with a remote consultant. The system would then send an invitation to the remote consultant. If accepted the remote consultant would be able to view the screen that is being displayed to the technician. Through a set of software collaboration tools, the user and the consultant could discuss the culture plate images, have an audio or video connection to one another, and mark up and discuss each presented image in real time. This consultation would allow the user to consult with an expert in a field to help determine the proper reading and diagnosis for the culture plate being analyzed.

Selecting Colonies During a Consultation Session

Embodiments relate to systems and methods for selecting a colony or other feature from a culture plate after review by the user and consultant. In one embodiment the culture plate is a petri dish and the system provides a variety of selection tools adapted to electronically select specific colonies for later processing. The selection tool may be a modified mouse cursor configured to allow for the selection of one or more colony locations on a culture plate image displayed on colony selection display screen of a culture reading system. In use, the system provides an interface that allows a user to conveniently select particular colony locations from one or more images taken of the culture plate. The system can further provide an interface that allows a user to share one or more culture plate images or user interface display screens to one or more devices. By providing back-end processing, the system can detect, and prevent, the user from selecting colony locations that don't meet predefined criteria. A selected colony location can be used by a user or instrumentation to perform a physical removal of a colony on the culture plate that corresponds to the selected colony location.

In one embodiment, the system determines if the colony location being selected is too close to an adjacent colony location that has already been selected. Thus, if a user attempts to select a colony location that is within a predetermined boundary of another selected colony location, the on-screen selection tool may indicate that such a selection is not available. In one embodiment the selection tool may change from a target indicator, to a red circle with a strike-through line to indicate that the chosen colony location is not available for selection. In another embodiment, the on-screen selection tool may change into other or different geographic indicia to indicate that the selection is not available. This process prevents the user from selecting a colony location that is too close to another colony location. A culture plate may include multiple organisms and adjacent colonies may represent different organisms. Restricting a user from selecting a colony location that is too close to another colony location can prevent removal of an undesired organism or a mixing of organisms when the adjacent colony locations correspond to different organisms. In some embodiments, the system also detects if the user is attempting to select colony locations that are adjacent other features of the culture plate, such as an edge, lip, or other protrusion from the culture plate. This features protects an electronic colony picker that is configured to contact the colony corresponding to the chosen colony location from striking or impinging on features of the culture plate.

FIG. 1 depicts a schematic view of an illustrative embodiment of a colony selection system 100. The colony selection system 100 includes a culture reading system 110, an incubation system 120, and picking instrumentation 130.

The incubation system 120 includes an incubator 122 and an imaging device 124. The incubator 122 can be configured to house and incubate one or more culture plates containing microorganisms and media for culturing the growth of the microorganisms. The imaging device 124 can be configured to capture and store images of the culture plates housed within the incubator 122. In some embodiments, the incubation system 120 is a ReadA Compact incubator.

The incubation system 120 can be configured to communicate with the culture reading system 110 via wired or wireless communication, cell communication, Bluetooth®, ZigBee®, LAN, WLAN, RF, IR, or any other communication method or system known in the art. For example, the incubation system 120 can be configured to transmit images of culture plates housed within the incubator 122 to the culture reading system 110.

In some embodiments, the incubation system 120 can be configured to transmit images of culture plates housed within the incubator 122 to an external database or image file storage system. The external database or image file storage system can be configured to transmit the images to the culture reading system 110 for use.

The culture reading system 110 includes a processor 102, a memory 104, an input 106 and a display 108. The memory 104, which can include both read-only memory (ROM) and random access memory (RAM), can be configured to provide instructions and data to the processor 102. For example, the memory 104 can store one or more modules that store data values defining instructions to configure processor 102 to perform functions of the culture reading system 110. As shown in FIG. 1, the memory 104 includes a selection tool module 112 that includes instructions that configure the processor 102 to perform selection tool functions as described herein. The memory 104 can also be configured to store images of culture plates received from the incubation system 120. The memory can further include a consultation module that includes instructions that configure the processor to perform consultation functions as described herein.

The display 108 can be configured to display data from the memory 104 and data received from the input 106. The input 106 can include one or more devices that allow a user to input data into the culture reading system 110. For example, the input 106 can include a keyboard, a mouse, and/or a touch screen in connection with the display 108. The input 106 and display 108 can operate to form a user interface presented on the display 108. The user interface can include one or more interactive display screens which provide culture plate data to a user and allow for data selection and manipulation.

In an illustrative embodiment of the present invention, the culture reading system 110 can be configured to display one or more culture plate images on the user interface provided on the display 108. In some embodiments, the culture reading system 110 can be configured to display a plurality of culture plate images simultaneously. The culture plate images can be retrieved from the memory 104, received from the incubation system 120, and/or received from another external device. The culture reading system 110 can allow for selection and/or manipulation of one or more of the plate images via the user interface presented on the display 108.

Colony Selection

In an illustrative embodiment of the present invention, the culture reading system 110 can facilitate selection of one or more colony locations on a culture plate image, wherein each colony location represents the location of a colony of biological material on the culture plate to which the image corresponds based on instructions stored within the selection tool module 112. For example, the culture reading system 110 can be configured to display an interactive colony selection display screen on the display 108 in response to a colony selection initiation event, such as a command from a user via the input 106.

In some embodiments, the selection tool module 112 is configured to cause the culture reading system 110 to provide a selection tool within the colony selection display screen for the selection of colony locations. The selection tool can be a cursor configured to allow for the selection of one or more colonies locations on a culture plate image displayed on colony selection display screen of the culture reading system 110. The position of the selection tool on the colony selection display screen can be manipulated using the input 106.

In some embodiments, the culture reading system 110 can be configured to determine the location of the culture plate image on the colony selection display screen. For example, the culture reading system 110 can determine or assign geographical coordinates for the culture plate image. The culture reading system 110 can also be configured to determine the location of the selection tool. For example, the culture reading system 110 can determine the geographical coordinates of the selection tool as compared to the geographical coordinates of the culture plate image. In some embodiments, the selection tool is configured to become visible when a cursor for interacting with the user interface scrolls over the culture plate image. For example, the cursor may change in appearance to become the selection tool when positioned over the culture plate image.

In some embodiments, the selection tool can allow for the selection of colony locations on the culture plate image that correspond to colonies of interest on the culture plate to which the image corresponds, such as colonies desired for use in diagnostic testing. The culture reading system 110 can be configured to correlate a selected colony location with coordinates on the culture plate shown in the culture plate image at which a picking tool, such as a pipetting tool, can be applied to pick up the desired colony. For example, each selected colony location can be stored as coordinates from a known/fixed position on the culture plate. In some embodiments, each selected colony location is stored as coordinates from the center of the culture plate. In some embodiments, each selected colony location can also be stored with a number indicating the order in which the colony location was selected. In some embodiments, the order in which the colony locations were selected corresponds to the order for picking the desired colonies from the culture plate. In some embodiments, the selection tool module 112 is configured to cause the culture reading system 110 to mark a selected colony location on the culture plate image with a visual icon or graphical indicia. The visual icon and/or coordinates correlated with the selected colony location can provide guidance to a user or automated picking tool for picking up a desired colony from the culture plate.

In some embodiments, desired colonies can be picked from a culture plate by the picking instrumentation 130. Picking instrumentation 130 can include an automated platform that robotically controls a picking tool 132 to pick up, pipette, or otherwise remove a desired colony from a culture plate. The culture reading system 110 can be configured to transmit data representing the coordinates of the desired colonies based on the colony location selections made using the selection tool or an image of the culture plate including markings at the locations of the desired colonies. The culture reading system 110 can be configured to communicate with the picking instrumentation 130 via wired or wireless communication, cell communication, Bluetooth®, ZigBee®, LAN, WLAN, RF, IR, or any other communication method or system known in the art. The picking instrumentation 130 can be configured to use the picking tool on the culture plate at the coordinates received from the culture reading system 110 or at the position of the markings shown on the image of the culture plate provided by the culture reading system 110. In some embodiments, the picking instrumentation 130 can be configured to align a culture plate image received from the culture reading system in the same orientation as the culture plate in order to match the coordinates and/or markings of selected colonies on the culture plate image with the desired colonies on the culture plate prior to pipetting. For example, the picking instrumentation 130 can be configured to run software that compares the orientation of the culture plate with that of the culture plate image and aligns the culture plate image so that the selected colony markers are in alignment with the desired colonies on the culture plate.

In some embodiments, the selection tool on the colony selection display screen can be shaped and sized to account for the shape and size of the picking tool 132 and/or a mechanical tolerance of the picking tool 132. For example, an outer edge of the selection tool can be shaped and sized to indicate a range of positions on the culture plate at which the picking tool 132 may pick the culture if the picking instrumentation 130 is provided the coordinates represented by a colony location selected using the selection tool. In other words, the selection tool can be shaped and sized such that any of the contents shown on the culture plate image within the outer edge of the selection tool may be picked by the picking tool 132 if a colony location selection is made at the location of the selection tool.

Some locations on the colony selection display screen may be invalid for colony selection. In some embodiments, the culture reading system 110 can be configured to determine invalid colony selection locations based on instructions from the selection tool module 112. Invalid colony selection locations can include colony selection locations that may lead to failed or erroneous pipetting by the picking tool 132. For example, it may be undesirable to select a colony location in which the tolerance of the picking tool 132 can allow for the picking tool to strike an edge of the culture plate or a culture plate divider. It can also be undesirable to select a colony location for a culture plate that is in a proximity to a previously selected colony location of the culture plate that, based on the tolerance of the picking instrumentation 130, can allow for the same colony to be picked by the picking tool 132 as that of the previously selected colony location.

In an illustrative embodiment, the selection tool module 112 can be configured to cause the culture reading system 110 to determine the location of one or more culture plate features that can act as potential sources of error, such as a culture plate edge, a culture plate divider, a previously selected colony, for example, using image processing software. The memory 104 can store a table of possible errors relating to the features of the culture plate. In some embodiments, the culture reading system 110 can be configured to determine the geographical coordinates of the culture plate features that can act as potential sources of error. The selection tool module 112 can further be configured to cause the culture reading system 110 to compare the location of the potential sources of error with the location of the selection tool. For example, the culture reading system 110 can be configured to compare the geographical coordinates of the selection tool with the geographical coordinates of one or more of the culture plate features. The selection tool module 112 can also be configured to cause the culture reading system 110 to determine when the selection tool overlays a potential source of error. For example, the culture reading system 110 can be configured to determine when there is a risk that the picking tool 132 will strike the edge of the culture plate, for example, when the section of the culture plate image representing the edge of the culture plate is positioned within the interior of the outer edge of the selection tool. The culture reading system 110 can also be configured to determine when there is a risk that the picking tool 132 will pick the same colony for two colony location selections, for example, when a marker indicating the previous colony location selection is positioned within the interior of the outer edge of the selection tool. The culture reading system 110 can also be configured to determine when there is a risk that the picking tool 132 will be deployed at a position outside of the culture plate based on a comparison of the location of the selection tool and the location of the edge of the culture plate and/or the interior of the culture plate.

In some embodiments, the selection tool module 112 can be configured to cause the culture reading system 110 to determine coordinate locations of all potential colony location selections on the culture plate image, for example, using image processing software. The culture reading system 110 can determine coordinate locations for each location on the culture plate image that corresponds to a colony on the culture plate. The culture reading system 110 can also determine which locations on the culture plate image that correspond to a colony on the culture plate do not risk an invalid colony selection. In some embodiments, the culture reading system 110 can be configured to identify an organism to which a colony corresponds or a difference between colonies depicted on the culture plate image indicating that the colonies correspond to different organisms, e.g., different color or shape on differential media types, for example, using image processing software. In some embodiments, the culture reading system 110 can be configured to allow for a selection of colony locations corresponding to colonies of a particular organism. In some embodiments, the culture reading system 110 can be configured to prevent selection of a colony locations corresponding to one type of organism if the colony selection tool is currently configured to select locations of a different type. In some embodiments, the selection tool can be configured to allow for a selection of an isolate number indicating a colony corresponding to a particular organism and a marking of one or more colonies with the isolate number. The culture reading system can prevent selection of colony locations that correspond to colonies corresponding to a different particular organism unless a different isolate number is selected.

In some embodiments, the selection tool can be configured to change appearance to provide a visual indication as to whether a valid colony location selection can be performed at a current location of the selection tool. For example, the size, shape, and/or color of the selection tool can change based on the location of the selection tool in comparison to various contents shown on the culture plate image, such as the sources of error described herein. For example, the selection tool can be configured to change appearance to indicate that the selection tool is positioned within the interior of the culture plate within the culture plate image. The selection tool can also be configured to change appearance to indicate that the selection tool is positioned outside of the edges of the culture plate within the culture plate image. The selection tool can also be configured to change appearance to indicate that the selection tool is positioned over the edges of the culture plate or a divider within the culture plate as shown on the culture plate image. In some embodiments, the selection tool can change appearance to indicate that the selection tool is positioned over a previously selected colony.

In some embodiments, the selection tool module 112 can be configured to cause the culture reading system 110 to prohibit selection of a colony location if it is determined that the colony location may result in an error of the picking instrumentation 130. For example, the culture reading system 110 can be configured to prohibit selection of a colony location if it is determined that the colony location is outside of the edge of the culture plate, overlaps the edge of the culture plate or a divider within the culture plate, or overlaps a previously selected colony location.

Figure 2:
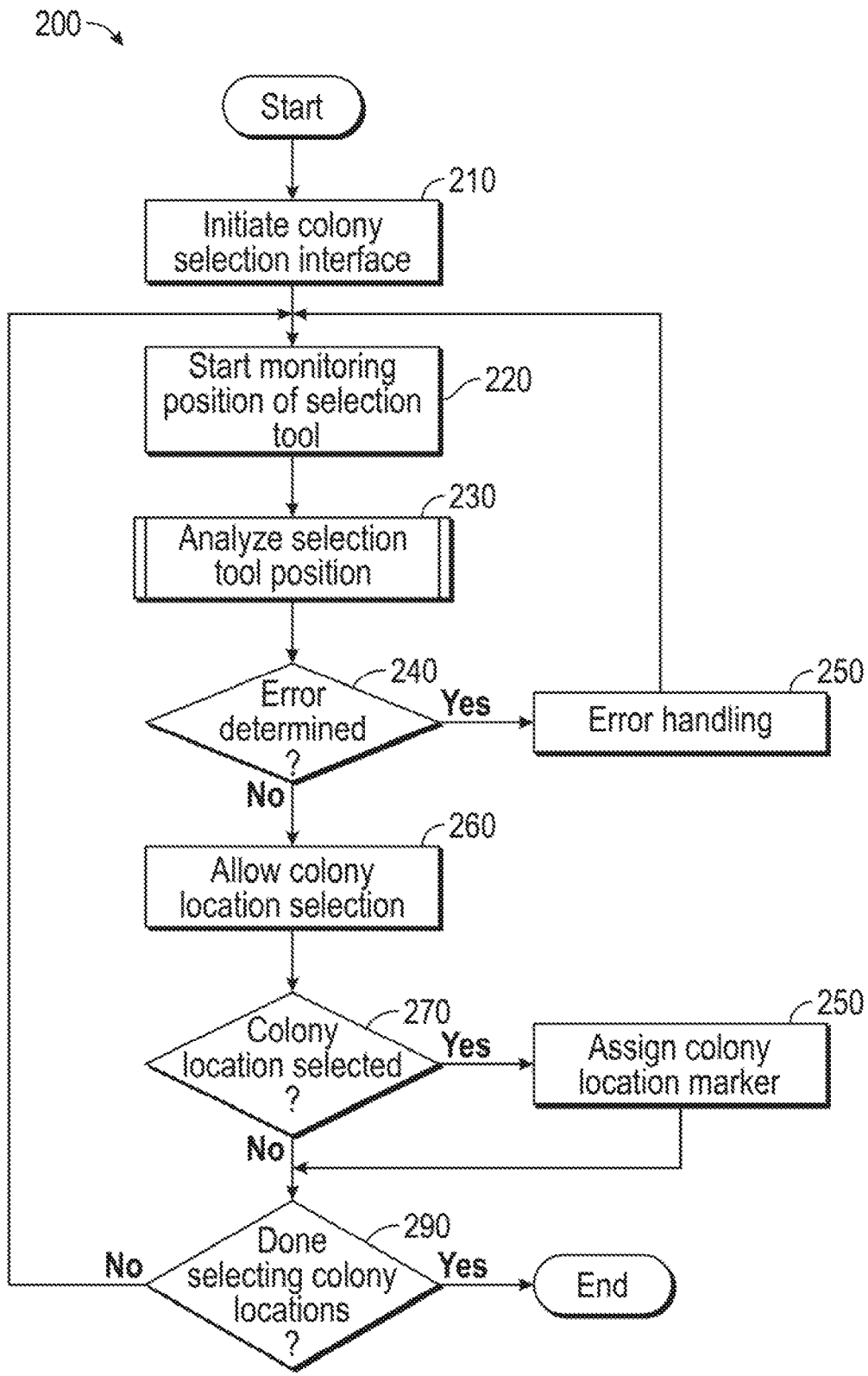
FIG. 2 depicts a flowchart of an embodiment of selecting colony locations in accordance with an illustrative embodiment of the present invention.

FIG. 2 depicts a flowchart of a process 200 of an illustrative embodiment of a method for selection of colony locations using a culture reading system such as culture reading system 110. The process 200 begins at a step 210, wherein a colony selection interface is initiated. A colony selection interface can include one or more display screens on a display, such as display 108, that allow for the selection of colony locations on an image of a culture plate. The colony selection interface can also include a selection tool for the selection of colony locations. As described above, the selection tool can be a cursor configured to move across the display and to allow for the selection of one or more colony locations on a culture plate image displayed on the colony selection interface. The colony selection interface may be part of a culture reading software application providing various options for analyzing and manipulating one or more culture plate images. The colony selection interface may be initiated by navigating to the colony selection interface through the culture reading software application.

After initiation of the colony selection interface, the process 200 moves to a step 220 wherein the position of the selection tool on the display starts to be monitored. The position of the selection tool can be monitored by a processor, such as processor 102, running a software application. The processor can monitor the position of the selection tool on the display or the position of the selection tool relative to a reference point on the culture plate image. The selection tool can be shaped and sized to overlay a desired colony depicted on the culture plate image. The selection tool can also be shaped and sized to account for the shape and size of a picking tool for pipetting a colony from the culture plate, such as picking tool 132, and/or a mechanical tolerance of a picking tool being operated by an automated pipetting system, such as picking instrumentation 130. Accordingly, the picking tool may extend over a range of coordinates on the culture plate image. The processor can monitor each coordinate overlaid by the selection tool at a given time. The processor can also monitor a center coordinate representing the center of the selection tool at a given time. In some embodiments, the processor can monitor the coordinates of an outer edge of the selection tool at a given time.

After the position of the selection tool starts to be monitored, the process 200 moves to a process step 230, wherein the position of the selection tool is analyzed. The position of the selection tool can be analyzed by a processor, such as processor 102, running a software application. In some embodiments, analysis of the position of the selection tool includes a comparison between the location of the selection tool and the location of one or more features of the culture plate shown on the culture plate image. For example, in some embodiments, analysis of the position of the selection tool includes a comparison of the position of the selection tool to the position of an edge of the culture plate, a divider of the culture plate, and/or a previously selected colony location on the culture plate image. The processor can be configured to determine that there is an error associated with the position of the selection tool if the position of the selection tool overlays a feature of the culture plate that is a potential source of error for picking a desired colony from the culture plate. For example, the processor can be configured to determine that there is an error associated with the selection tool if the position of the selection tool is outside of the edge of the culture plate or overlays one or more of the edge of the culture plate, a divider of the culture plate, and a previously selected colony location on the culture plate image. Such selection tool locations may represent locations at which a picking tool may not be able to pick the appropriate colony due to obstruction, by the edge of the culture plate or divider, for example, or due to a risk of pipetting a colony from a previously selected colony location. In some embodiments, each coordinate covered by the selection tool is compared to the location of the one or more features of the culture plate. In some embodiments, a center coordinate of the selection tool is compared to the location of the one or more features of the culture plate and it is determined whether any of the one or more features of the culture plate are within a predetermined distance of the center of the selection tool. The distance from the center of the selection tool can correspond to the outer edge of the selection tool as shown on the culture plate image.

After the position of the selection tool is analyzed, the process 200 moves to a decision step 240, wherein a decision is made whether an error has been determined at the position of the selection tool. If an error has been determined, the process 200 moves to a step 250, wherein error handling is performed. Error handling can include changing the appearance of the selection tool to indicate an error. For example, error handling can include changing the appearance of the selection tool to indicate that the selection tool is positioned outside of the edge of the culture plate, over the edge or divider of the culture plate, or over a previously selected colony location. In some embodiments, the shape, size, and or color of the selection tool can change to indicate an error. Error handling may also include preventing a selection of a colony location when an error is determined. After error handling, the process 200 returns to step 220.

If a decision is made at step 240 that an error did not occur, the process 200 moves to a step 260, wherein a selection of a colony location is allowed at the position of the selection tool. In some embodiments, when a colony location selection is allowed, a user can make a colony location selection using an input, such as input 106. In some embodiments, a colony location selection can be performed by a software application.

After selection of a colony location is allowed, the process 200 moves to a decision step 270, wherein a decision is made whether a colony location is selected. If a determination is made that a colony location is selected, the process 200 moves to a step 280, wherein a colony location marker is assigned to the selected colony. The colony location marker can include a colony location number to allow for tracking and distinguishing of particular colonies. In some embodiments, each colony location marker receives a number based on the order in which the colony location was selected. In some embodiments, the colony location marker can receive an isolate number indicating an organism corresponding to the colony corresponding to the colony location. Multiple colonies locations can be selected for the same organism. Consequently, multiple colony location markers can include the same isolate number. The colony location marker can also correspond to the shape and size of the selection tool. The colony location marker can correspond to the shape and size of the picking tool and/or a mechanical tolerance of an automated pipetting system. The shape and size of the marker can allow for a comparison between the position of the marker and the selection tool as described with respect to step 230 to determine if the position of the selection tool overlays the position of the marker.

After a colony marker is assigned at step 280 or if it is determined that a colony location is not selected at step 270, the process 200 moves to a decision step 290, wherein a decision is made if colony locations are finished being selected. It can be determined that colony locations are done being selected based on an input by a user. In some embodiments, it can be determined that colony locations are done being selected if a maximum number of colony locations have been selected. The maximum number of colony locations may be specific to the type of culture plate or to a planned diagnostic testing procedure for the organisms on the culture plate.

If the colony locations are not finished being selected, the process 200 returns to step 220. If the colony locations are done being selected, the process 200 concludes.

Figure 3:
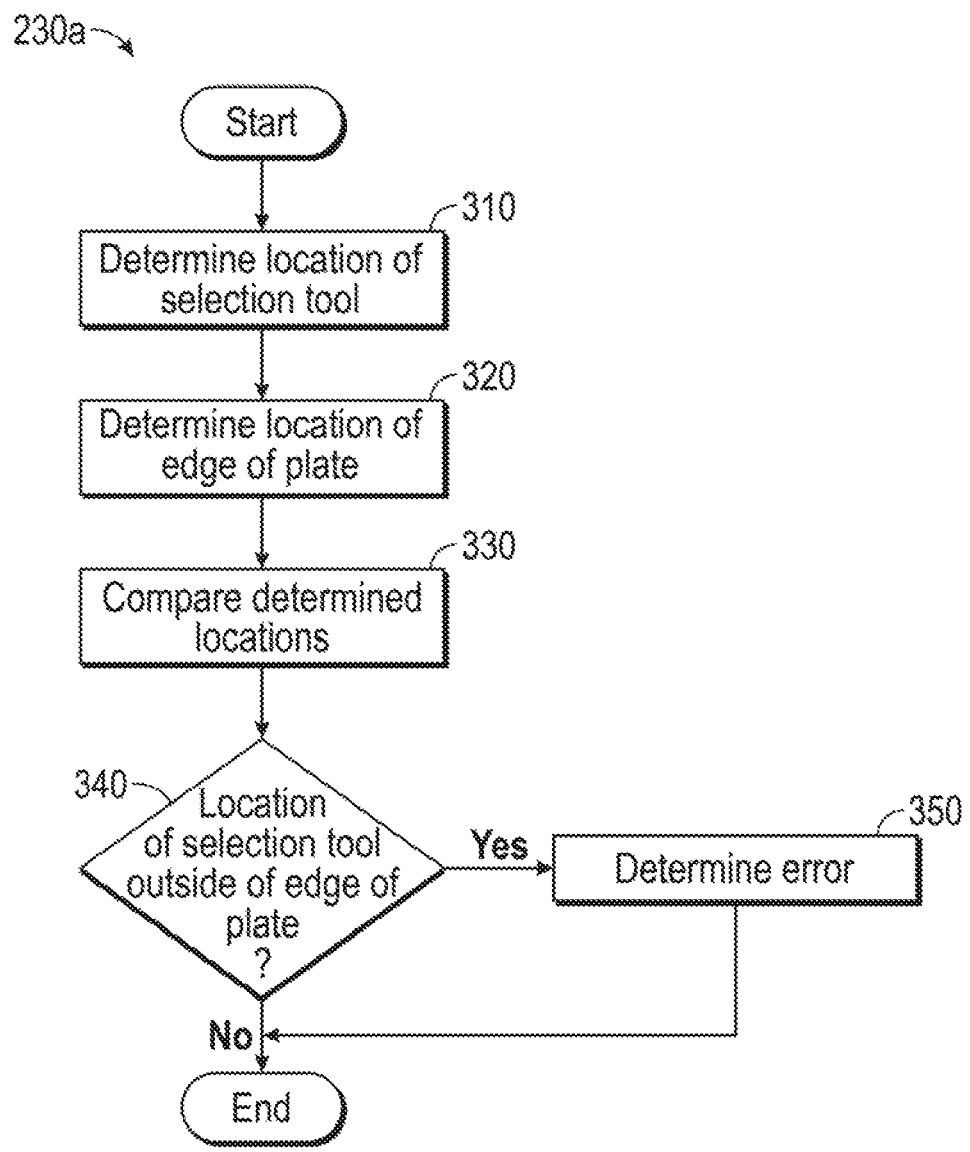
FIG. 3 depicts a flowchart of an embodiment of analyzing the position of a selection tool in accordance with an illustrative embodiment of the present invention.
Figure 4:
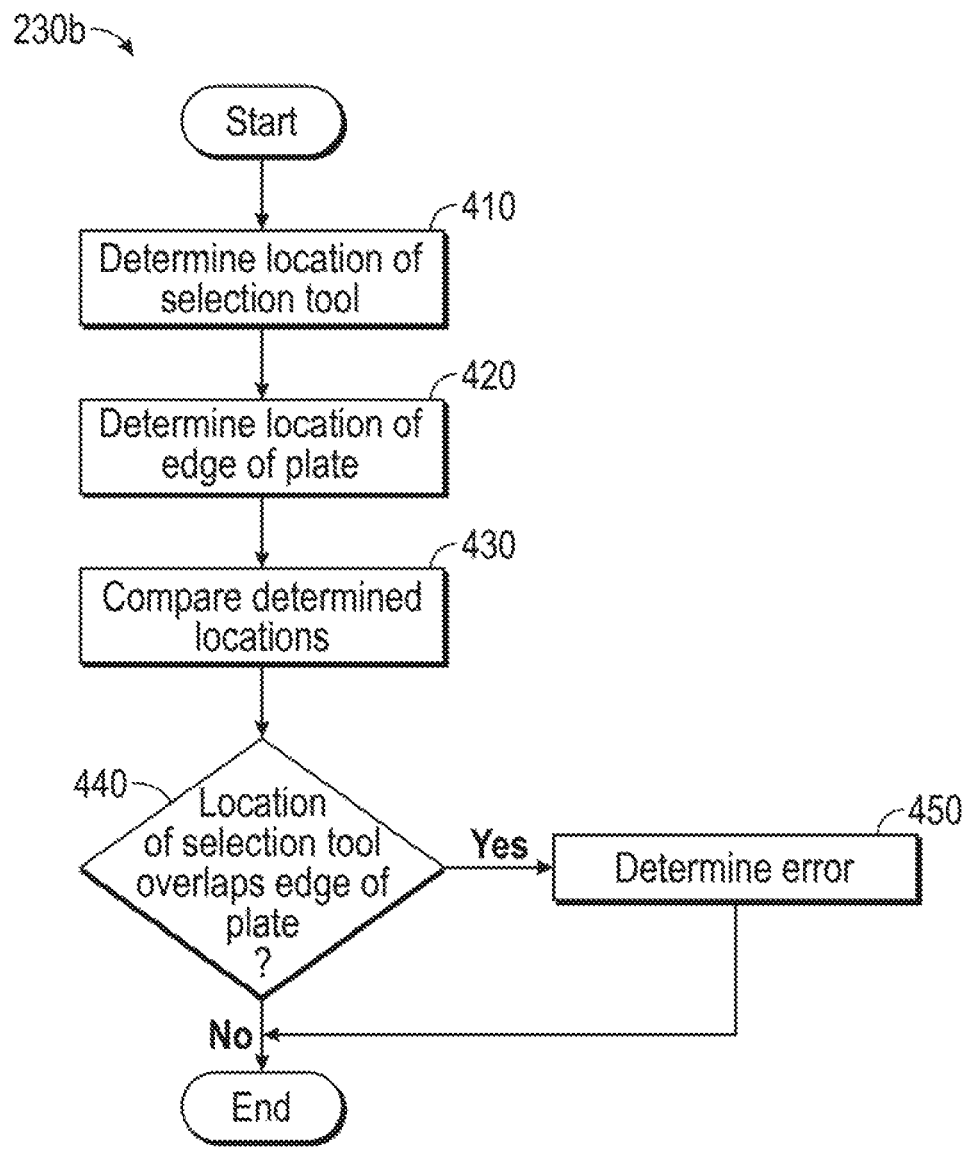
FIG. 4 depicts a flowchart of an embodiment of analyzing the position of a selection tool in accordance with an illustrative embodiment of the present invention.
Figure 5:
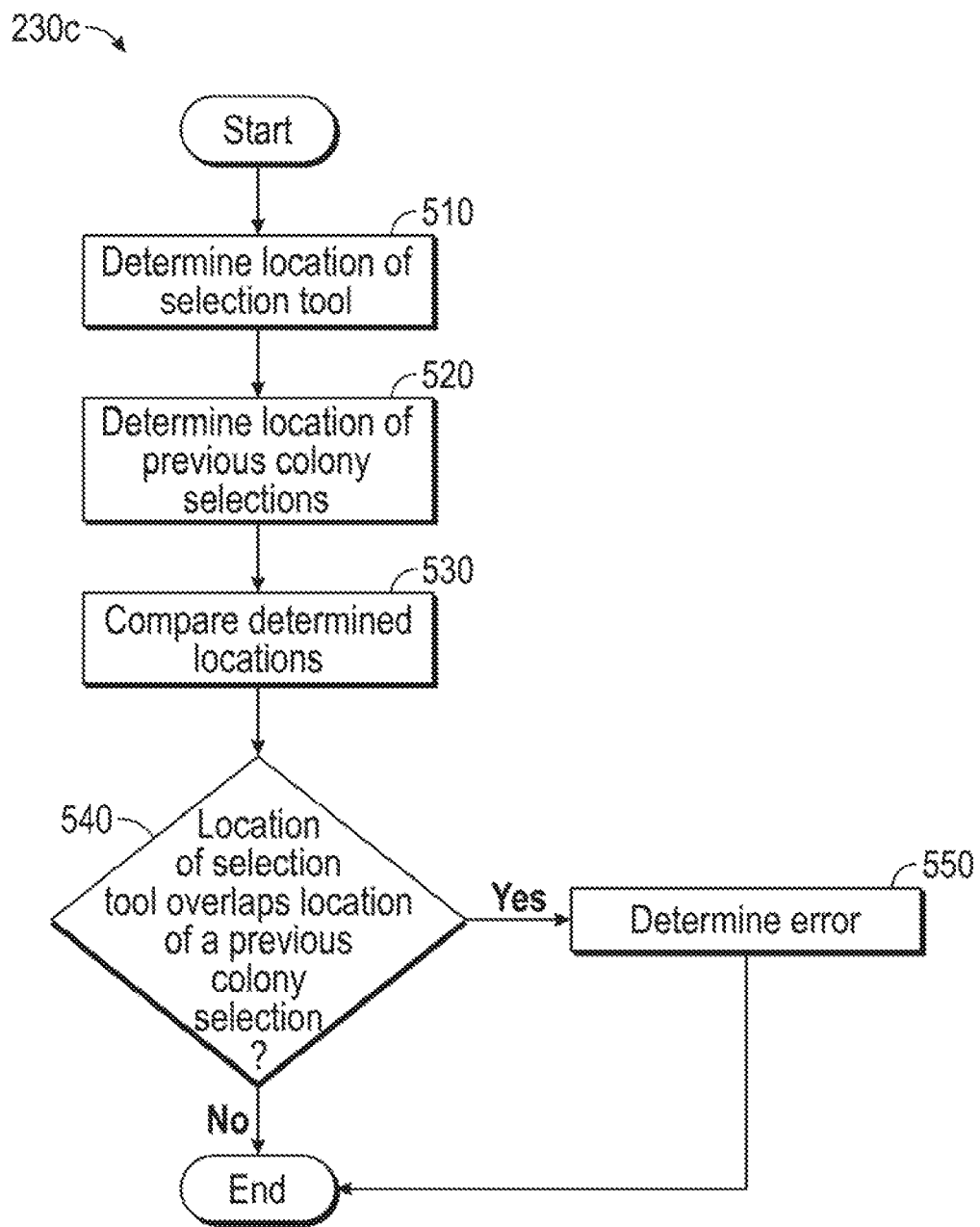
FIG. 5 depicts a flowchart of an embodiment of analyzing the position of a selection tool in accordance with an illustrative embodiment of the present invention.

FIGS. 3-5 each depict a flowchart of different illustrative embodiments of the process 230 for analyzing the position of the selection tool. For clarity, the embodiments of the process 230 shown in FIGS. 3-5 will be referred to as processes 230*a*, 230*b*, and 230*c*, respectively.

The process 230*a* provides an example of analyzing the position of the selection tool to determine if the selection tool is positioned outside of the peripheral edge of the culture plate as represented on the culture plate image. As shown in FIG. 3, the process 230*a* begins with a step 310 wherein the location of the selection tool is determined. As described above, the selection tool can extend over a range of coordinates, one or more of which can be determined. The location of the selection tool can be determined by the processor running a software application.

After the location of the selection tool is determined, the process 230*a* moves to a step 320, wherein the location of the edge of the culture plate depicted in the culture plate image is determined. As described above, the location of the edge of the culture plate can be determined by a processor running image processing software that analyzes the features of the culture plate and correlates those features with the image being displayed to the user.

After the location of the edge of the culture plate is determined, the process 230*a* moves to a step 330, wherein the location determined for the selection tool is compared to the location determined for the culture plate edge.

After the location determined for the selection tool and the location determined for the culture plate edge are compared, the process 230*a* moves to a decision step 340, wherein a decision is made whether the location of the selection tool is outside of the edge of the culture plate. If the location of the selection tool is outside of the edge of the culture plate, the process 230*a* moves to a step 350 wherein an error is determined. After an error is determined at step 350, or if the location of the selection tool is not outside of the edge of the culture plate, the process 230*a* concludes.

As shown in FIG. 4, the process 230*b* begins with a step 410 wherein the location of the selection tool is determined. As described above, the selection tool can extend over a range of coordinates, one or more of which can be determined. The location of the selection tool can be determined by a processor running a software application.

The process 230*b* provides an example of analyzing the position of the selection tool to determine if the selection tool is positioned over an internal border of the culture plate as represented on the culture plate image, such as a divider or edge of the culture plate. After the location of the selection tool is determined, the process 230*b* moves to a step 420, wherein the location of the edge of the culture plate depicted in the culture plate image is determined. As described above, the location of the edge of the culture plate can be determined by a processor running image processing software to calculate this feature of the culture plate and correlate it with the image being displayed.

After the location of the edge of the culture plate is determined, the process 230*b* moves to a step 430, wherein the location determined for the selection tool is compared to the location determined for the culture plate edge.

After the location determined for the selection tool and the location determined for the culture plate edge are compared, the process 230*b* moves to a decision step 440, wherein a decision is made whether the location of the selection tool overlays the edge of the culture plate. If the location of the selection tool overlays the edge of the culture plate, the process 230*b* moves to a step 450 wherein an error is determined. After an error is determined at step 450, or if the location of the selection tool does not overlay the edge of the culture plate, the process 230*b* concludes.

The process 230*c* provides an example of analyzing the position of the selection tool to determine if the selection tool is positioned over a previously selected colony location. As shown in FIG. 5, the process 230*c* begins with a step 510 wherein the location of the selection tool is determined. As described above, the selection tool can extend over a range of coordinates, one or more of which can be determined. The location of the selection tool can be determined by a processor running a software application.

After the location of the selection tool is determined, the process 230*c* moves to a step 520, wherein the location of any previously selected colony locations is determined. The location of the previously selected colony locations can be determined by a processor running a software application.

After the location of the previously selected colony locations is determined, the process 230*b* moves to a step 530, wherein the location determined for the selection tool is compared to the location determined for the previously selected colony locations.

After the location determined for the selection tool and the location determined for the previously selected colony locations are compared, the process 230*c* moves to a decision step 540, wherein a decision is made whether the location of the selection tool overlays the previously selected colony locations. If the location of the selection tool overlays the previously selected colony locations, the process 230*c* moves to a step 550 wherein an error is determined. After an error is determined at step 550, or if the location of the selection tool does not overlay previously selected colony locations, the process 230*c* concludes.

Although processes 230*a*, 230*b*, and 230*c* are shown as separate processes, it should be understood that two or more of the processes can be performed in combination or parallel in a process step 230. While specific potential sources of error are addressed in processes 230*a*, 230*b*, and 230*c*, it should be recognized that similar processes can be run for any other potential source of error on a culture plate, for example, by determining the location of the selection tool, determining the location of a potential source of error, comparing the location of the selection tool to the location of the potential source of error, and determining an error if the location of the selection tool overlays the potential source of error. In some embodiments, determining a location of the selection tool include determining geographical coordinates of the selection tool in comparison to geographical coordinates of the culture plate image. Determining the location of a potential source of error can include determining the geographical coordinates of a culture plate feature that may cause a potential error shown on the culture plate image. Comparing the location of the selection tool to the location of the potential source of error can include comparing the geographical coordinates of the selection tool to the geographical coordinates of the culture plate feature shown on the culture plate image. Determining an error can include referencing a table of possible errors related to features of the culture plate. The table of possible errors may be stored in a memory, such as memory 104. The table of possible errors can include, for example, entries for the selection tool overlapping a previously selected colony, the selection tool overlapping a protrusion on the culture plate image such as an edge or divider, and the selection tool being positioned outside of the culture plate shown on the culture plate image.

Figure 6:
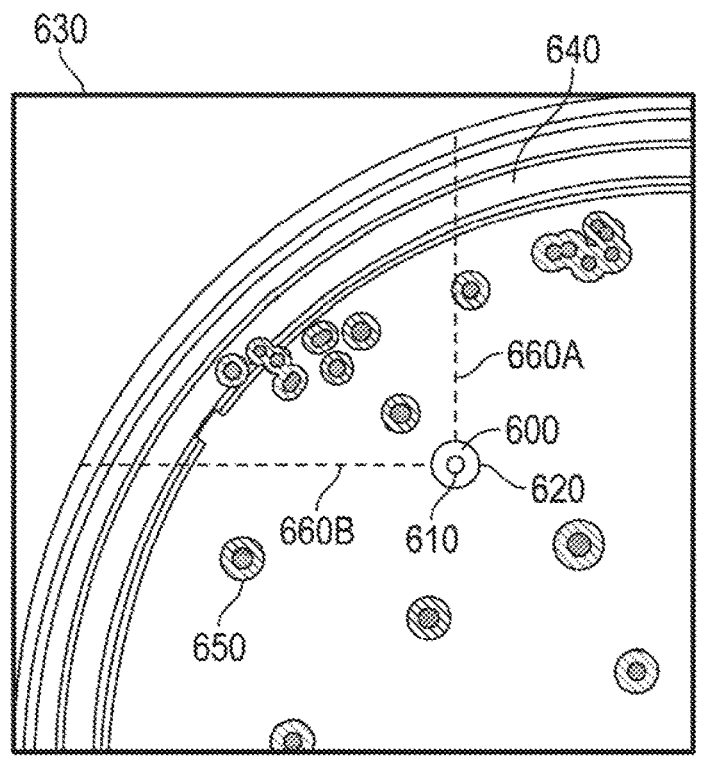
FIG. 6 depicts a selection tool positioned over an image of a culture plate in accordance with an illustrative embodiment of the present invention.

FIGS. 6-9 depict embodiments of selection tools in accordance with the present invention. FIG. 6 depicts an embodiment of a selection tool 600 positioned over an image 630 showing a culture plate 640 having a plurality of colonies, including colony 650. The selection tool 600 includes an inner ring 610 and an outer ring 620. In some embodiments, the inner ring can shaped and sized to substantially match the shape and size of a tip of a pipetting tool, such as picking tool 132. The interior of the inner ring can represent an intended location of pipetting by the picking tool on the culture plate 640.

As described above, the picking tool may be controlled by an automated platform, such as picking instrumentation 130. The picking tool as controlled by the automated platform can have a tolerance of error from the desired location of pipetting. The outer ring 620 can correspond to the tolerance of error of the picking tool from the desired location of pipetting. As described herein, the position of the outer ring 620 can be analyzed to determine if there is a possibility of error such as, for example, striking an obstruction or pipetting the same colony based on two selected colony locations.

The selection tool 600 can further include guidelines 660A and 660B, extending from the selection tool 600 along the y-axis and x-axis, respectively. The guidelines 660A and 660B can provide additional visual aids for positioning of the selection tool 600 on the image 630. The guidelines 660A and 660B may also provide a contrast to the culture plate image in order to improve the visibility of the selection tool on the culture plate image.

Figure 7:
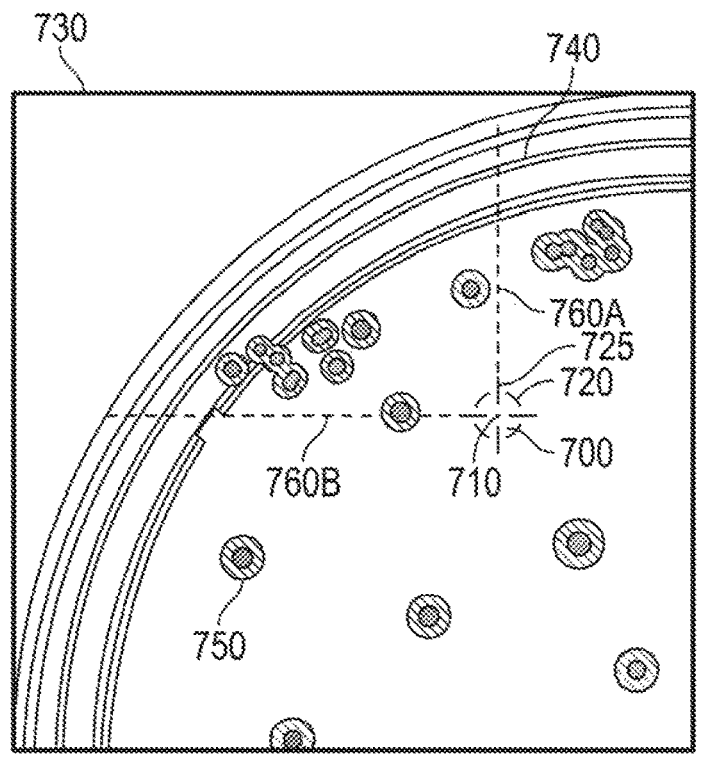
FIG. 7 depicts a selection tool positioned over an image of a culture plate in accordance with an illustrative embodiment of the present invention.

FIG. 7 depicts an embodiment of a selection tool 700 positioned over an image 730 showing a culture plate 740 having a plurality of colonies, including colony 750. The selection tool includes a center dot 710 positioned at a center point of the selection tool 700, a dashed outer ring 720, and a plurality of crosshair lines 725. The center dot 710 can represent an intended location of a center of a picking tool, such as picking tool 132, for pipetting on the culture plate 740.

As described above, the picking tool may be controlled by an automated platform, such as picking instrumentation 130. The picking tool as controlled by the automated platform can have a tolerance of error from the desired location of pipetting. The outer ring 720 can correspond to the tolerance of error of the picking tool from the desired location of pipetting. As described herein, the position of the outer ring 720 can be analyzed to determine if there is a possibility of error such as, for example, striking an obstruction or pipetting the same colony based on two selected colony locations.

The selection tool 700 can include four crosshair lines 725. One pair of crosshair lines 725 can be positioned on the x-axis, each crosshair line being positioned on opposite sides of the center dot 710. A second pair of crosshair lines 725 can be positioned on the y-axis, each crosshair lines being positioned on opposite sides of the center dot 710. The crosshair lines can provide a visual aid for positioning of the selection tool 700. In comparison to the inner ring 610 of FIG. 6, the crosshairs may provide improved visibility to a colony location below the selection tool, The selection tool 700 can further include guidelines 760A and 760B, extending from the selection tool 700 along the y-axis and x-axis, respectively. The guidelines 760A and 760B can provide additional visual aids for positioning of the selection tool 700 on the image 730. The guidelines 760A and 760B may also provide a contrast to the culture plate image in order to improve the visibility of the selection tool on the culture plate image.

Figure 8:
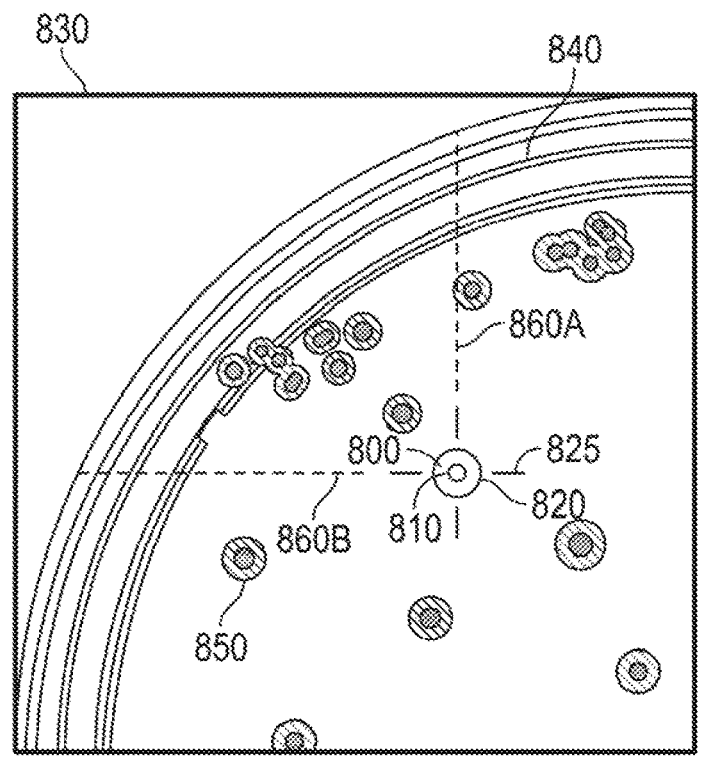
FIG. 8 depicts a selection tool positioned over an image of a culture plate in accordance with an illustrative embodiment of the present invention.

FIG. 8 depicts an embodiment of a selection tool 800 positioned over an image 830 showing a culture plate 840 having a plurality of colonies, including colony 850. The selection tool 800 includes an inner ring 810, an outer ring 820, and a plurality of crosshair lines 825. In some embodiments, the inner ring can shaped and sized to substantially match the shape and size of a tip of a picking tool, such as picking tool 132. The interior of the inner ring can represent an intended location of pipetting by the picking tool on the culture plate 840.

As described above, the picking tool may be controlled by an automated platform, such as picking instrumentation 130. The picking tool as controlled by the automated platform can have a tolerance of error from the desired location of pipetting. The outer ring 820 can correspond to the tolerance of error of the picking tool from the desired location of pipetting. As described herein, the position of the outer ring 820 can be analyzed to determine if there is a possibility of error such as, for example, striking an obstruction or pipetting the same colony based on two selected colony locations.

The selection tool 800 can include four crosshair lines 825. One pair of crosshair lines 825 can be positioned on the x-axis, each crosshair line being positioned on opposite sides of the outer ring 820. A second pair of crosshair lines 825 can be positioned on the y-axis, each crosshair lines being positioned on opposite sides of the outer ring 820. The crosshair lines can provide a visual aid for positioning of the selection tool 800. The selection tool 800 can further include guidelines 860A and 860B, extending from the selection tool 800 along the y-axis and x-axis, respectively. The guidelines 860A and 860B can provide additional visual aids for positioning of the selection tool 800 on the image 830. The guidelines 860A and 860B may also provide a contrast to the culture plate image in order to improve the visibility of the selection tool on the culture plate image.

Figure 9:
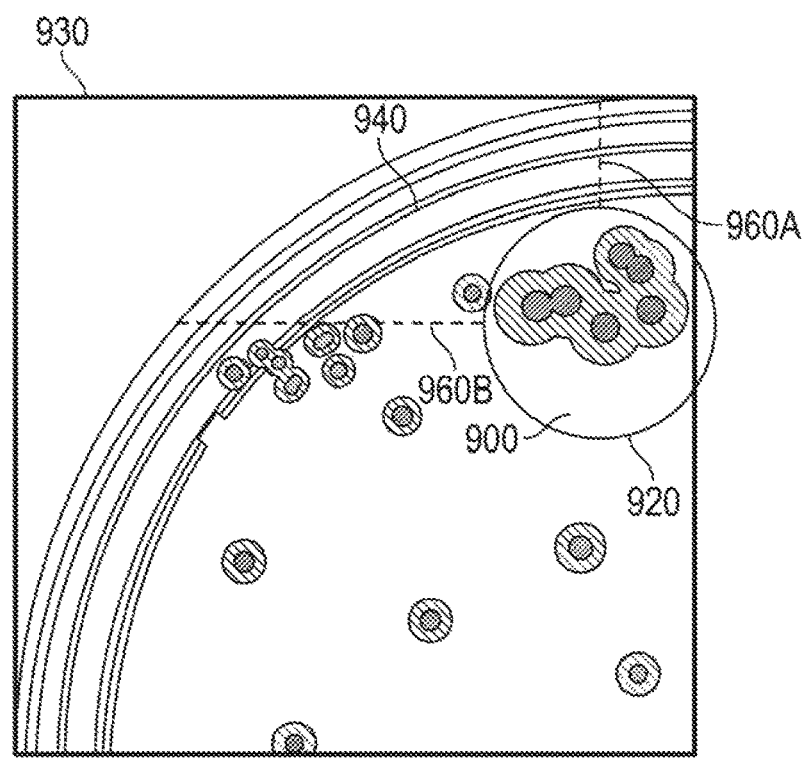
FIG. 9 depicts a selection tool positioned over an image of a culture plate in accordance with an illustrative embodiment of the present invention.

FIG. 9 depicts an embodiment of a selection tool 900 positioned over an image 930 showing a culture plate 940 having a plurality of colonies. The selection tool 900 can include a ring 920. The interior of the ring 920 can show a magnified view of the section of the image 930 below the ring 920. As described above, the picking tool may be controlled by an automated platform, such as picking instrumentation 130. The picking tool as controlled by the automated platform can have a tolerance of error from the desired location of pipetting. The ring 920 can correspond to the tolerance of error of the picking tool from the desired location of pipetting. As described herein, the position of the outer ring 920 can be analyzed to determine if there is a possibility of error such as, for example, striking an obstruction or pipetting the same colony based on two selected colony locations. In some embodiments, the position of the outer ring 920 is itself magnified, such that the position of the outer ring 920 as shown on the image 930 may appear larger than the coordinates for the position of the outer ring 920 that are analyzed to determine a possibility of error.

The selection tool 900 can further include guidelines 960A and 960B, extending from the selection tool 900 along the y-axis and x-axis, respectively. The guidelines 960A and 960B can provide additional visual aids for positioning of the selection tool 900 on the image 930. The guidelines 960A and 960B may also provide a contrast to the culture plate image in order to improve the visibility of the selection tool on the culture plate image.

In some embodiments, a colony selection interface allows a selection between a plurality of different selection tool configurations, such as those shown in FIGS. 6-9. It should be understood that configurations shown for the colony selection tool in FIGS. 6-9 are not limiting. In accordance with the present invention, a colony selection tool can be any size and shape suitable for selecting a colony location and for providing a visual indication of potential sources of error. For example, features from any of the embodiments shown in FIGS. 6-9 can be combined to form a colony selection tool.

Figure 10:
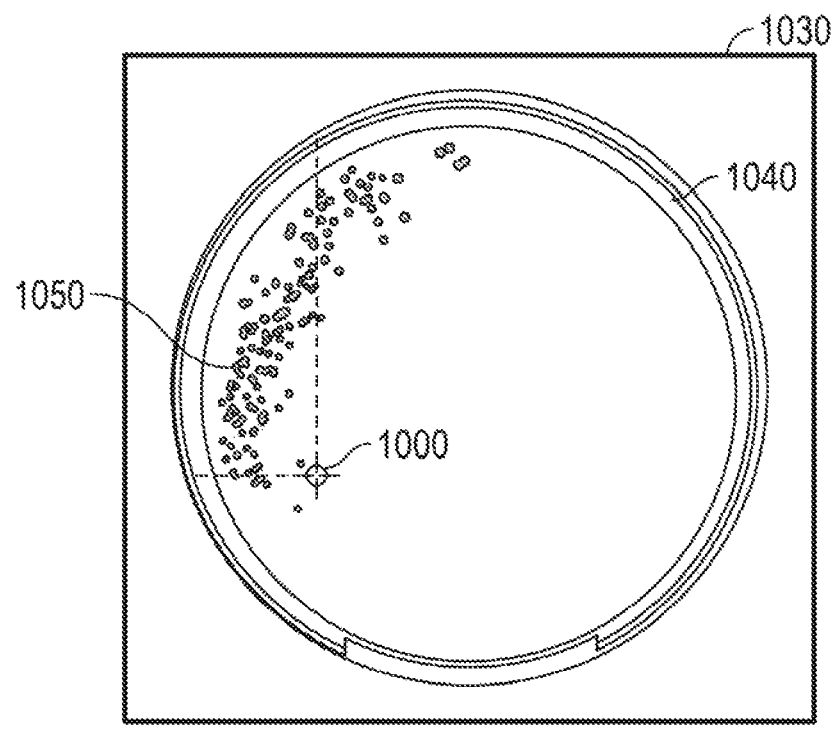
FIG. 10 depicts a selection tool positioned over an image of a culture plate in accordance with an illustrative embodiment of the present invention.
Figure 11:
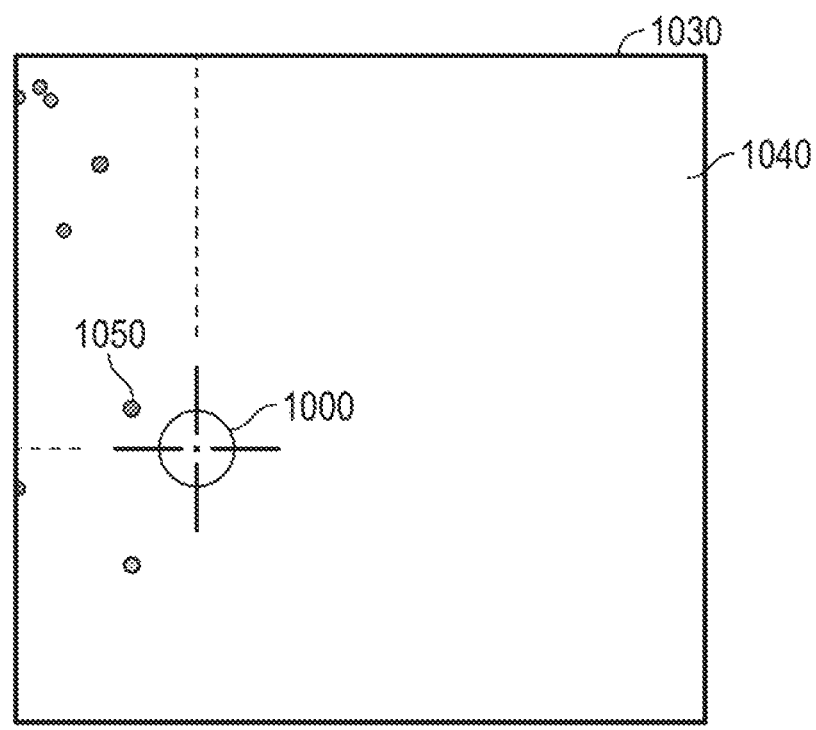
FIG. 11 depicts a selection tool positioned over an image of a culture plate in accordance with an illustrative embodiment of the present invention.

FIG. 10 depicts an illustrative embodiment of a selection tool 1000 positioned over an image 1030 showing a culture plate 1040 having a plurality of colonies 1050. FIG. 11 shows a magnified view of a section of the image 1030 shown in FIG. 10. In an illustrative embodiment, the colony selection interface displaying the image 1030 can allow for manipulation of the image 1030, for example by changing the magnification of the image 1030. As demonstrated by FIGS. 10 and 11, the selection tool 1000 can be configured to change in size to accommodate for the change in magnification of the image 1030. The magnification of the selection tool 1000 can be performed so that the selection tool is indicative of a mechanical tolerance of picking instrumentation, such as picking instrumentation 130, at each degree of magnification.

Figure 12:
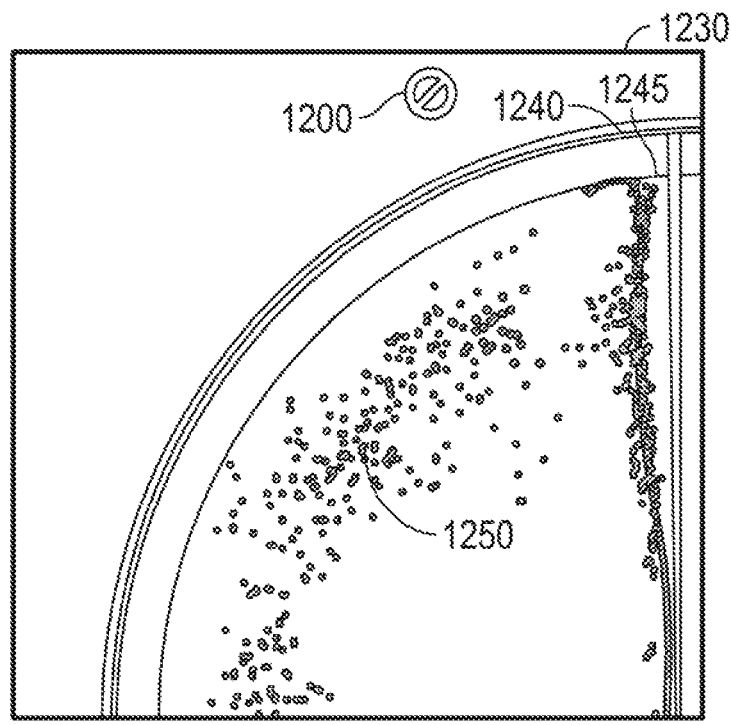
FIG. 12 depicts a selection tool positioned over an image of a culture plate in accordance with an illustrative embodiment of the present invention.

FIG. 12 depicts an illustrative embodiment of a selection tool 1200 positioned over an image 1230 showing a culture plate 1240 having a plurality of colonies 1250. The culture plate 1240 has a culture plate edge 1245. As shown in FIG. 12, the selection tool 1200 is positioned outside of the culture plate edge 1245. FIG. 12 demonstrates an example of error handling, such as that described in step 250 of FIG. 2, when the location of the selection tool is outside of the edge of the culture plate 1245, as described, for example, with respect to step 340 of FIG. 3. As shown in FIG. 12, the selection tool 1200 is shown as a circle with a diagonal line running through it. This shape of the selection tool 1200 indicates that the selection tool is in a location that may result in an error if selected. The shape of the selection tool 1200, as shown in FIG. 12, is configured to be different than the shape of the selection tool 1200 if positioned within the edge 1245 of the culture plate 1200.

Figure 13:
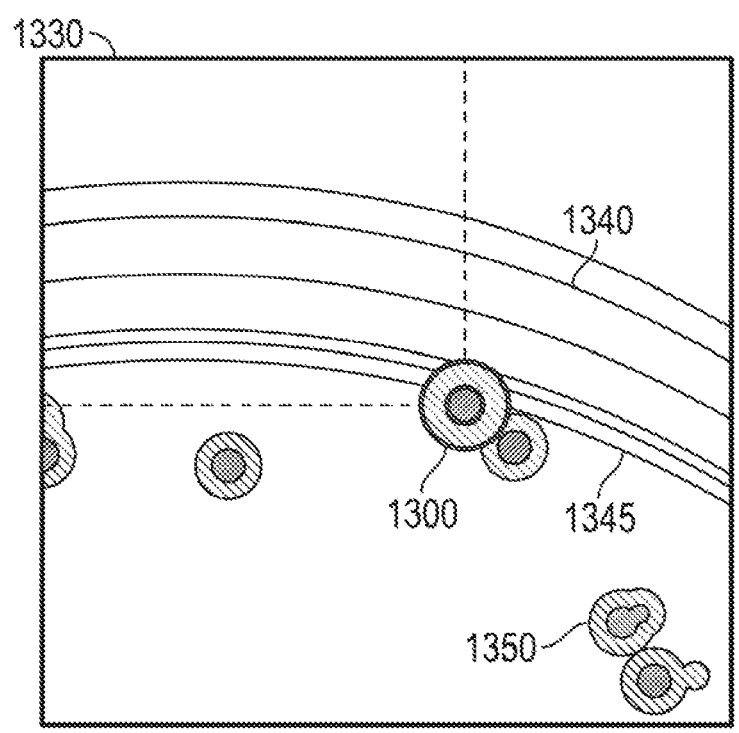
FIG. 13 depicts a selection tool positioned over an image of a culture plate in accordance with an illustrative embodiment of the present invention.
Figure 14:
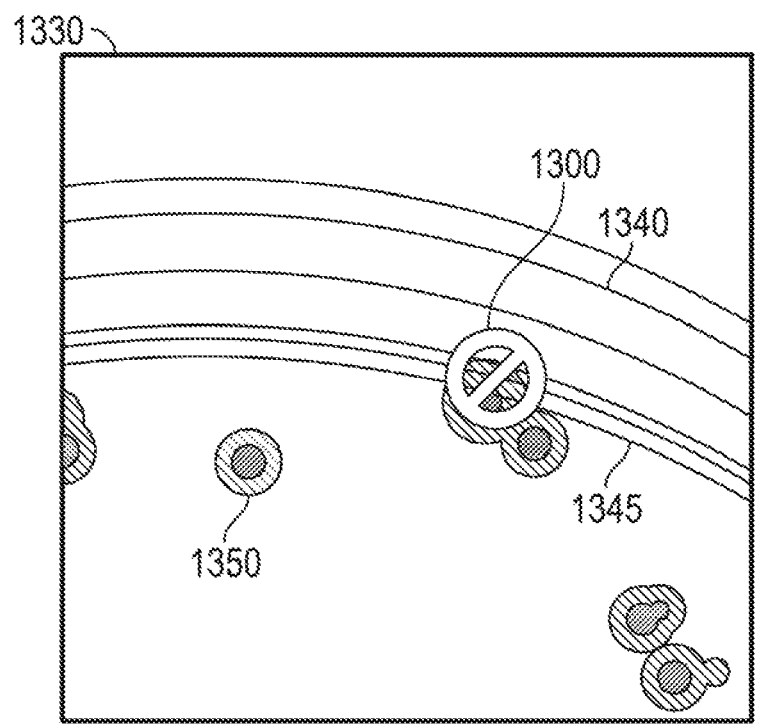
FIG. 14 depicts a selection tool positioned over an image of a culture plate in accordance with an illustrative embodiment of the present invention.

FIG. 13 depicts an illustrative embodiment of a selection tool 1300 positioned over an image 1330 showing a culture plate 1340 having a plurality of colonies, including colony 1350. The culture plate 1340 has a culture plate edge 1345. FIG. 13 shows the selection tool 1300 positioned near an inner wall of the edge 1345. FIG. 14 shows the selection tool 1300 positioned over the image 1330 after the selection tool 1300 has been advanced farther over the edge 1345. As shown in FIG. 14, the shape of the selection tool 1300 has changed in comparison to that shown in FIG. 13. The change in the shape of the selection tool 1300 between FIGS. 13 and 14 demonstrates an example of error handling, such as that described in step 250 of FIG. 2, when the location of the selection tool overlays the edge 1345 of the culture plate 1300, as described, for example, with respect to step 440 of FIG. 4.

Figure 15:
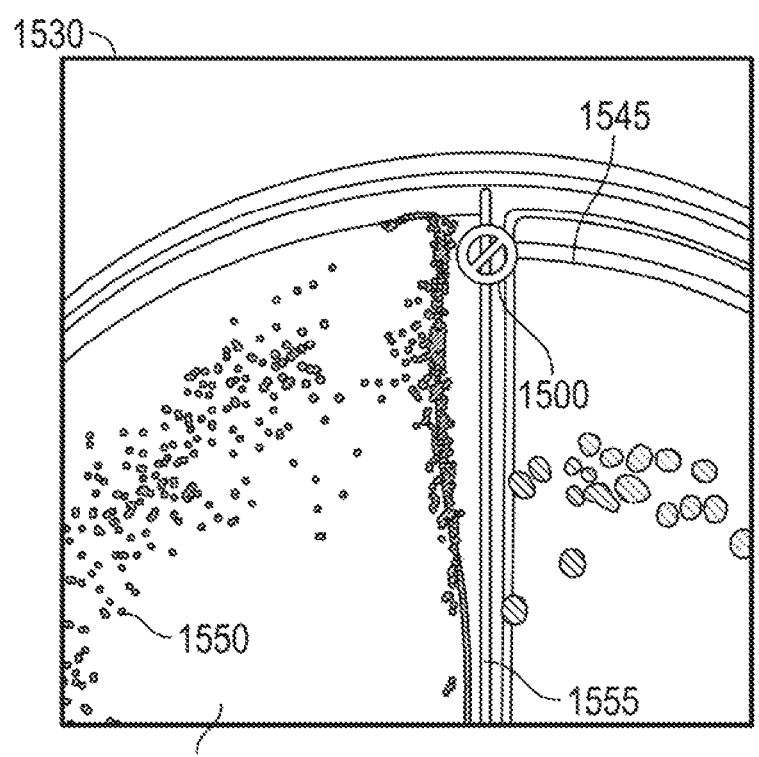
FIG. 15 depicts a selection tool positioned over an image of a culture plate in accordance with an illustrative embodiment of the present invention.

FIG. 15 depicts an illustrative embodiment of a selection tool 1500 positioned over an image 1530 showing a culture plate 1540 having a plurality of colonies, including colony 1550. The culture plate 1540 includes a culture plate edge 1545 and a divider 1555. FIG. 15 demonstrates an example of error handling, such as that described in step 250 of FIG. 2, when the location of the selection tool overlays the position of the divider 1555. The shape of the selection tool 1500 is configured to indicate that the selection tool is in a location that may result in an error if selected.

Figure 16:
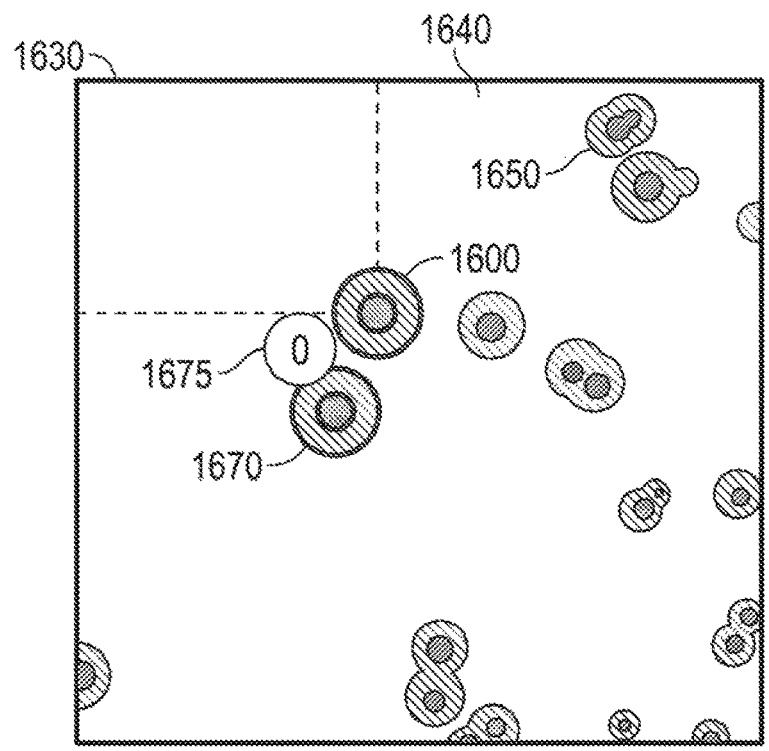
FIG. 16 depicts a selection tool positioned over an image of a culture plate in accordance with an illustrative embodiment of the present invention.

FIG. 16 depicts an illustrative embodiment of a selection tool 1600 positioned over an image 1630 showing a culture plate 1640 having a plurality of colonies, including colony 1650. FIG. 16 also shows a colony marker 1670 and a colony location marker number 1675 associated with the colony location marker 1670. The colony location marker 1670 can be substantially the same shape and size as the selection tool 1600. However, the colony location marker 1670 can be any shape and size sufficient for indicating the position of a colony. For example, the size and shape of the colony location marker 1670 can be similar to the size and shape of any of selection tool 600, selection tool 700, selection tool 800, and selection tool 900, or any combination thereof.

Figure 17:
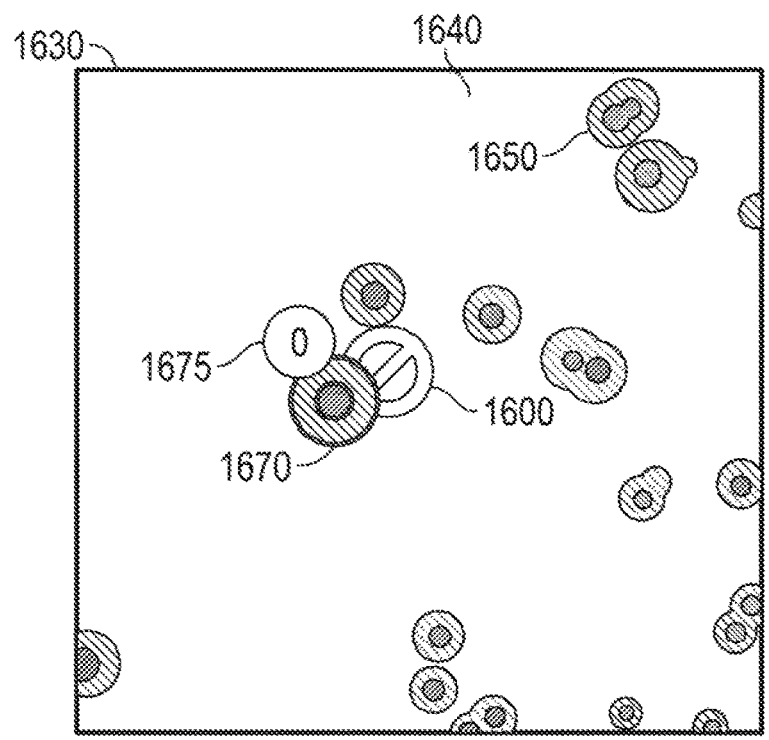
FIG. 17 depicts a selection tool positioned over an image of a culture plate in accordance with an illustrative embodiment of the present invention.

As described herein, colony location marker 1670 can represent a desired location that has been selected for pipetting by a picking tool, such as picking tool 132. The colony location marker 1670 can be sized and shaped to accommodate a tolerance of the picking tool. As described herein the selection tool 1600 is also sized and shaped to accommodate a tolerance of the picking tool. In FIG. 16, the selection tool 1600 is positioned apart from the marker 1670. FIG. 17 shows the selection tool 1600 positioned over the image 1630. In FIG. 17, the selection tool 1600 is positioned such that the outer edge of the selection tool 1600 overlays a section of the marker 1670. As shown in FIG. 17, the shape of the selection tool 1600 has changed in comparison to that shown in FIG. 16. The change in the shape of the selection tool 1600 between FIGS. 16 and 17 demonstrates an example of error handling, such as that described in step 250 of FIG. 2, when the location of the selection tool overlays a previously selection colony location, as described, for example, with respect to step 540 of FIG. 5.

Colony Consultation

In an illustrative embodiment, a culture plate image storage system, such as culture reading system 100, can be connected with an informatics network to facilitate consultation regarding one or more culture plate images across a plurality of devices. In some embodiments, for example, culture plate images stored by the culture plate image storage system can be accessible over an informatics system comprising a privately accessible computer network, such as an intranet. The informatics system can allow for the sharing of data between users accessing the informatics system on different devices. Devices can communicate with the informatics system, for example, via wired or wireless communication, cell communication, Bluetooth®, ZigBee®, LAN, WLAN, RF, IR, or any other communication method or system known in the art. In some embodiments, sharing data can be facilitated through a central server. In other embodiments, sharing of data can be performed using a peer-to-peer networking.

In some embodiments, the informatics system can facilitate the sharing of a user interface display screen and/or one or more culture plate images across a plurality of devices. The informatics system can further facilitate the concurrent display of a user interface display screen and/or one or more culture plate images across a plurality of devices. In some embodiments, the informatics system can facilitate the concurrent editing or annotation of a user interface display screen and/or one or more culture plate images across a plurality of devices. The user informatics system can further facilitate the sharing of audio and/or or video recordings or live audio and/or video transmission across a plurality of devices.

Figure 18:
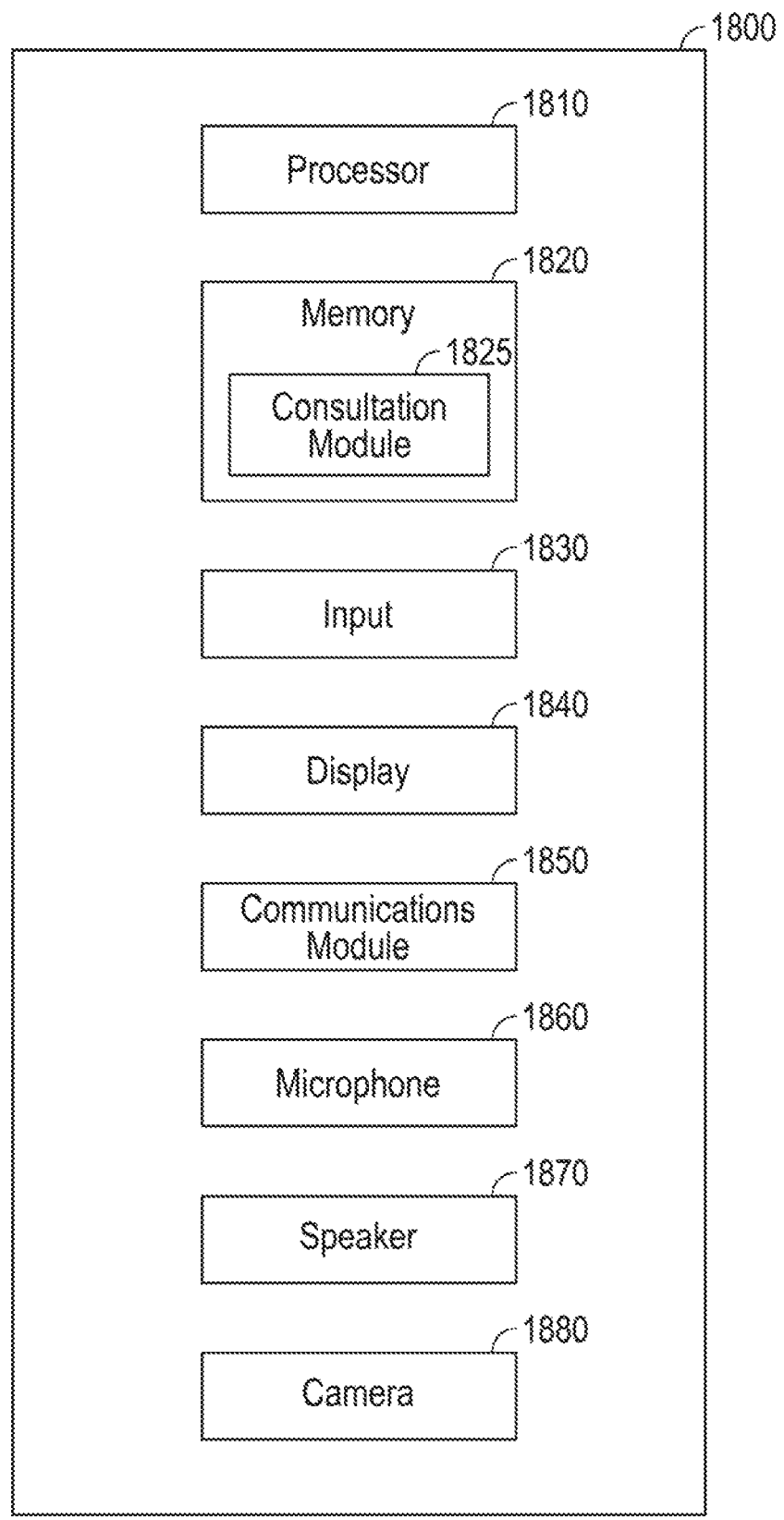
FIG. 18 depicts a schematic view of a device for use with an informatics system in accordance with an illustrative embodiment of the present invention.

FIG. 18 depicts an example of a device 1800 for use with the informatics system. The device 1800 can include a processor 1810, a memory 1820, an input 1830, and a display 1840. The memory 1820, which can include both read-only memory (ROM) and random access memory (RAM), can be configured to provide instructions and data to the processor 1810. For example, the memory 1820 can store one or more modules that store data values defining instructions to configure processor 1810 to perform functions of the culture reading system. For example, the memory 1820 can include a consultation module 1825 that includes instructions that configure the processor 1810 to perform consultation functions as described herein. The memory 1820 can also be configured to store images of culture plates received from the culture plate image storage system or other device and any associated metadata.

The display 1840 can be configured to display data from the memory 1820 and data received from the input 1830. The input 1830 can include one or more devices that allow a user to input data into the device. For example, the input can include a keyboard, a mouse, and/or a touch screen in connection with the display 1840. The input 1830 and display 1840 can operate to form a user interface presented on the display 1840. The user interface can include one or more interactive display screens which provide culture plate data to a user and allow for data selection and manipulation. The processor 1810 can be configured to process data received from the user interface.

In an illustrative embodiment, the device 1800 in connection with the informatics system can be configured to display one or more culture plate images on the user interface provided on the display 1840 and any annotations performed on the culture plate images. In some embodiments, the device can be configured to display a plurality of culture plate images simultaneously. The culture plate images can be retrieved from the memory 1820, received from the culture plate image storage system, and/or received from another external device. The informatics system can allow for selection and/or manipulation of one or more of the plate images via the user interface presented on the display 1840.

The informatics system can provide a user profile for each authorized user. Each user profile can be associated with a unique user ID and password. Each user profile can also be associated with a set of permissions that authorize the user to access particular data and perform particular functions within the informatics system and also restrict the user from accessing particular data and performing particular functions. Permissions can be assigned to each individual user as well as to different classifications of users. For example, some users may be technicians who are responsible for the processing of culture plates. Other users may be consultants who can be contacted by technicians to provide insight on particular topics.

The informatics system may also provide a user interface for each user, which may be different depending on the permissions of the user or the type of device through which the user is accessing the informatics system. A technician may have access to a user interface such as that described above with respect to FIGS. 1-17. The technician user interface may be configured to display one or more culture plate images and to allow the technician to perform one or more functions related to the culture plate image. For example, the user interface may be configured to allow the technician to select and/or mark one or more colonies on a culture plate image, as described above with respect to FIGS. 1-17 for example, order one or more tests to be performed on a culture plate associated with the culture plate image, or enter test results to associate the test results with the culture plate associated with the culture plate image. In some embodiments, when a technician selects a colony, the technician can optionally enter data to be associated with the colony, such as, for example, a type of colony, a description of what may be indicated by the colony, any questions about the colony, or any other relevant notes.

When processing a culture plate image using the user interface, a technician may desire to consult with one or more consultants about issues or questions related to the culture plate image. The informatics system can be configured to facilitate communication and the sharing of data, including sending and/or receiving data, between the technician and another system user who can act as a consultant via a communications module 1850. The consultant can be a user of the informatics system with access to a consultant user interface which can allow the consultant to receive a communication and data from another system user, a consultation technician such as a technician, and to respond to the other system user. Audio and video communications may be established to assist in the collaborative communication through the communications module 1850. The communications module 1850 can allow communication using wired or wireless communication, cell communication, Bluetooth®, ZigBee®, LAN, WLAN, RF, IR, or any other communication method or system known in the art. Audio communications may be recorded by a microphone 1860, which can be an internal microphone on the device which the user is using to connect to the informatics system or on an external microphone. In some embodiments, the device can include a speaker 1870 for emitting audio communications. Video communication may be recorded using a camera 1880, which can be a camera on the device through which the user is connecting to the informatics system or an external camera. Video recordings of the user interface display screen of a technician or consultant can be recorded and/or transmitted by software of the device on which the particular consultant or technician is accessing the informatics system. In some embodiments, the processor 1810 can be configured to associate one or more audio recordings or video recordings with one or more culture plate images. The processor 1810 may configured to instruct the communications module to transmit the one or more culture plate images and any audio recordings or video recordings associated with the one or more culture plate images to an external device or computer network.

The informatics system can facilitate both live consultation in which a consultation technician, such as a technician reading a culture plate image, and a remote consultant are communicating over the informatics system at the same time. In another embodiment, the informatics system provides a deferred consultation in which a consultation technician shares a communication via the user interface with a consultant to be processed and responded to at a later time.

Figure 19A:
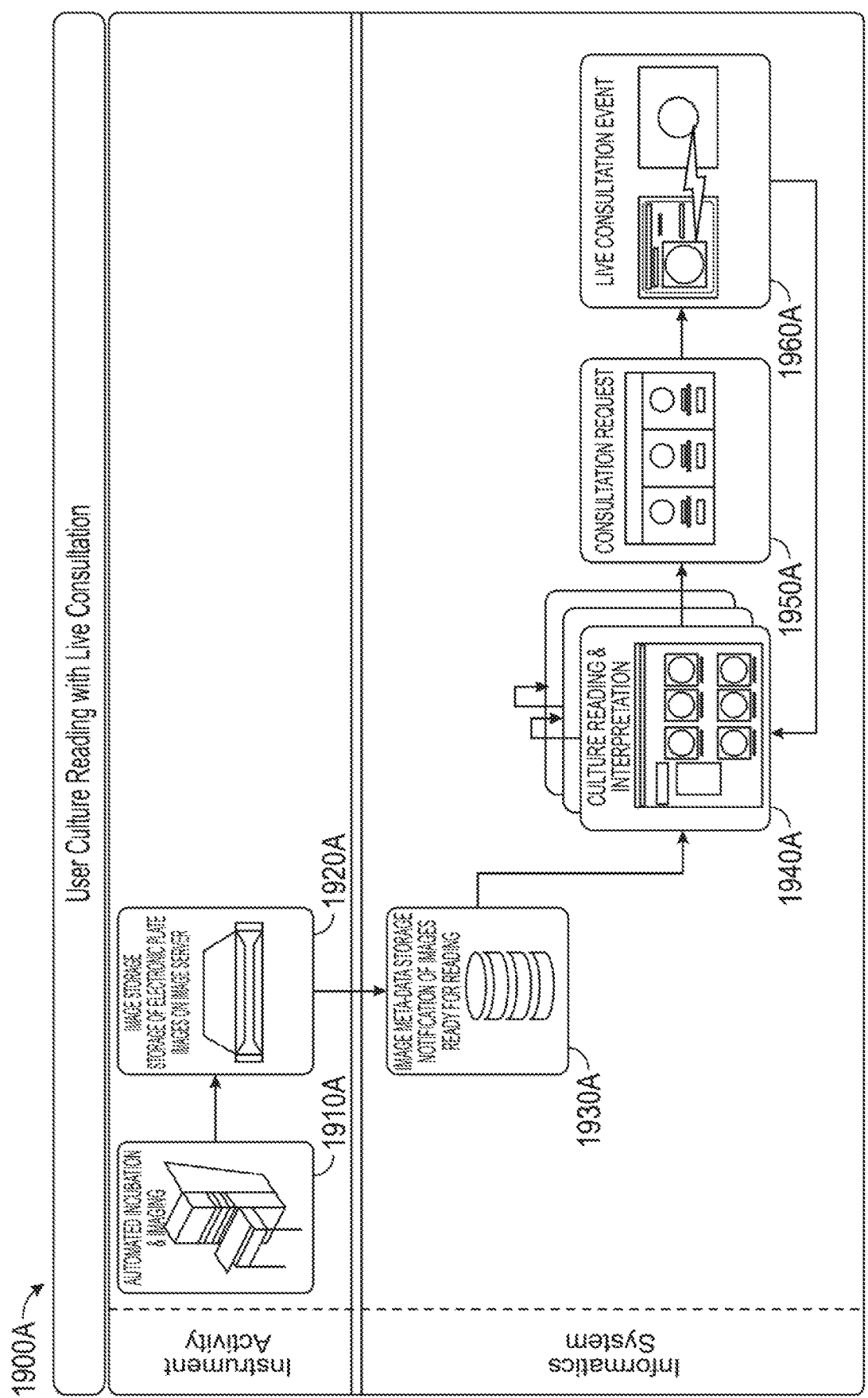
FIG. 19A depicts a workflow diagram providing an illustrative example of a process for performing a culture reading with a live consultation in accordance with an illustrative embodiment of the present invention.

FIG. 19A depicts a workflow diagram providing an illustrative example of a process 1900A for performing a culture reading with a live consultation in accordance with an embodiment of the present invention. The process 1900A begins with a first step 1910A of capturing a culture plate image using an automated incubation imaging system, such as the incubation system 120 of FIG. 1. After the culture plate image is capture, the culture plate image can then be transmitted to an image storage device, such as the culture reading system 110 of FIG. 1, and the process 1900A can move to a step 1920A wherein the culture plate image is stored by the image storage device.

After the culture plate image is stored by the image storage device, metadata associated with the culture plate image can be transmitted from the image storage device to an image metadata storage module of an informatics system, and the process 1900A can move to a step 1930A wherein the image metadata storage module can provide a notification to a technician that the culture plate image associated with the metadata is ready for a culture plate reading. In some embodiments, the informatics system can be configured to notify a particular user, such as a technician assigned to process a culture plate, or user group when metadata regarding an image corresponding to the culture plate is received by the informatics system, for example, to notify the technician or user group that a culture plate image is available for further processing. In some embodiments, the informatics system can include a list of images to be processed by the user or group of users. In some embodiments, the informatics system can be configured to notify the user or user group of one or more work activities to be performed on the image at the image storage system.

After the notification is provided to the technician, the process 1900A can move to a step 1940A, wherein culture plate reading and interpretation can be performed. The technician can access the informatics system to view the culture plate image on a display screen of a user interface of a device, such as device 1800. The user interface can further allow the technician to perform one or more actions related to processing of the culture plate represented by the culture plate image, such as, for example, selecting and/or marking colony locations, as described herein, ordering one or more tests to be performed on the culture plate, or entering test results to associate the test results with the culture plate image.

In the process 1900A, the technician may determine that a consultation with a consultant or group of consultants is desirable after reviewing the culture plate image. If the technician determines that a consultation is desirable, for example, if the technician requires assistance in making decisions regarding the disposition of a culture, the process 1900A can move to a step 1950A wherein the technician can transmit a consultation request for consultation with one or more system users or user groups, by selecting a software control on the user interface. After transmission of the consultation request, the process 1900A can move to a step 1960A, wherein the informatics system can initiate a live consultation event between the technician and the one or more system users or user groups. During the live consultation, the informatics system may allow the technician to share their user interface display screen or one or more culture plate images on their user interface display screen with the one or more users or user groups, such that the one or more users or user groups can view the user interface display screen of the technician or the one or more culture plate images on their own device(s), which can be, for example, the device 1800 as shown in FIG. 18.

Figure 19B:
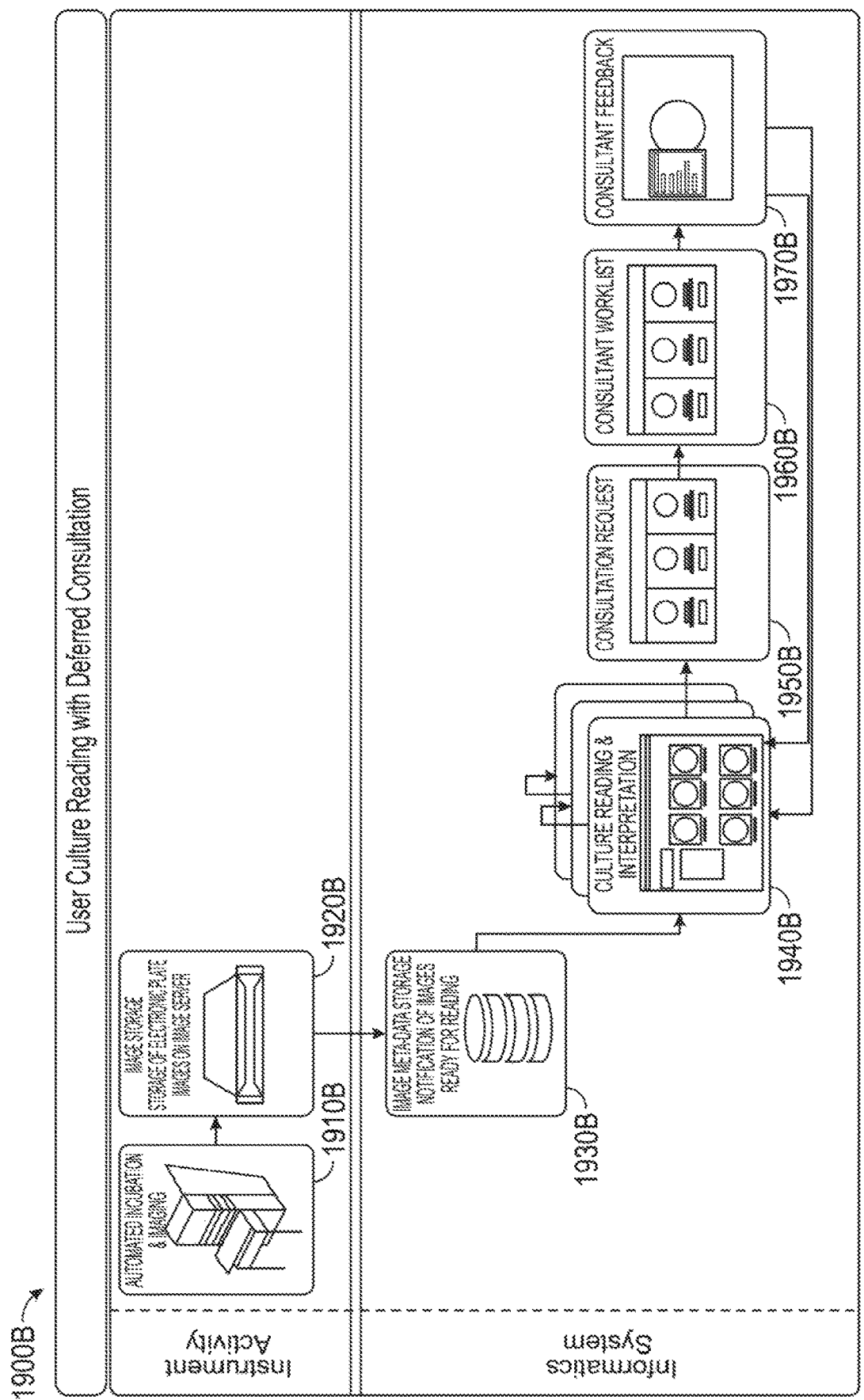
FIG. 19B depicts a workflow diagram providing an illustrative example of a process for performing a culture reading with a deferred consultation in accordance with an illustrative embodiment of the present invention.

FIG. 19B depicts a workflow diagram providing an illustrative example of a process 1900B for performing a culture reading with a deferred consultation in accordance with an embodiment of the present invention. The process 1900B begins with a first step 1910B of capturing a culture plate image using an automated incubation imaging system, such as the incubation system 120 of FIG. 1. After the culture plate image is capture, the culture plate image can then be transmitted to an image storage device, such as the culture reading system 110 of FIG. 1, and the process 1900B can move to a step 1920B wherein the culture plate image is stored by the image storage device.

After the culture plate image is stored by the image storage device, metadata associated with the culture plate image can be transmitted from the image storage device to an image metadata storage module of an informatics system, and the process 1900B can move to a step 1930B wherein the image metadata storage module can provide a notification to a technician that the culture plate image associated with the metadata is ready for a culture plate reading. In some embodiments, the informatics system can be configured to notify a particular user, such as a technician assigned to process a culture plate, or user group when metadata regarding an image corresponding to the culture plate is received by the informatics system, for example, to notify the technician or user group that a culture plate image is available for further processing. In some embodiments, the informatics system can include a list of images to be processed by the user or group of users. In some embodiments, the informatics system can be configured to notify the user or user group of one or more work activities to be performed on the image at the image storage system.

After the notification is provided to the technician, the process 1900B can move to a step 1940B, wherein culture plate reading and interpretation can be performed. The technician can access the informatics system to view the culture plate image on a display screen of a user interface of a device, such as device 1800. The user interface can further allow the technician to perform one or more actions related to processing of the culture plate represented by the culture plate image, such as, for example, selecting and/or marking colony locations, as described herein, ordering one or more tests to be performed on the culture plate, or entering test results to associate the test results with the culture plate image.

In the process 1900B, the technician may determine that a consultation with a consultant or group of consultants is desirable after reviewing the culture plate image. If the technician determines that a consultation is desirable, for example if the technician requires assistance in making decisions regarding the disposition of a culture, the process 1900B can move to a step 1950B wherein the technician can transmit a consultation request for consultation with one or more system users or user groups, by selecting a software control on the user interface. In some embodiments, the informatics system may allow the technician to share one or more screen shots of their user interface display screen, one or more videos of their user interface display screen, and/or one or more culture plate images with the user or user group as part of the consultation request. After transmission of the consultation request, the process 1900B can move to a step 1960B, wherein the informatics system can transmit or store the consultation request to a worklist or worklists of the one or more system users or user groups from which consultation is requested. After the consultation request is transmitted or stored to the worklist or worklists of the one or more system users or user groups from which consultation is requested, the consultation request can be selected from the worklist or worklists and the process 1900B can move to a step 1970B wherein feedback to the consultation request is provided by the one or more users or user groups from which consultation is requested. The one or more users or user groups from which consultation is requested can provide feedback on a device, such as device 1800 as shown in FIG. 18.

During a live consultation, as described with respect to process 1900A of FIG. 19A, or a deferred consultation, as described with respect to process 1900B of FIG. 19B, the informatics system can provide a plurality of communications and data sharing functionalities to each of a consultation technician, such as a technician, and a consultant, a user that receives a consultation request and accepts the consultation request, on their respective user interfaces. For example, in a live consultation, the informatics system may allow the technician to share their user interface display screen or one or more culture plate images on their user interface display screen with the consultant, such that the consultant can view the user interface display screen of the technician or the one or more culture plate images on their own device. In a deferred consultation, the informatics system may allow the technician to share one or more screen shots of their user interface display screen, one or more videos of their user interface display screen, and/or one or more culture plate images with the consultant. In some embodiments, the informatics system can facilitate audio and/or video communication between the technician and the consultant, either live or audio and/or video recordings. In some embodiments, the informatics system can provide annotation tools to one or more of the technician and the consultant on their respective user interfaces. For example, annotation tools may include markers, highlighters, drawing tools, comments, etc., that can be used to annotate a culture plate image. In some embodiments, an annotation can be associated with a culture plate image, for example, by a processor, such as processor 1810 as shown in FIG. 18. In some embodiments, a culture plate image and an annotation associated with the culture plate image can be transmitted to a computer network or an external device, for example, via a communications module such as communications module 1850 as shown in FIG. 18. In some embodiments, an annotation can be temporary, such that the annotation only appears during the consultation and is not permanently associated with a culture plate image. In some embodiments, an annotation may be stored with a copy of a culture plate image for later access. In some embodiments, an annotation may be stored with the culture plate image. In some embodiments, the informatics system may allow a consultant to control the user interface of the technician.

When initiating a live consultation or a deferred consultation, a consultation technician, such as a technician, can select one or more system users or system user groups to receive a consultation request. Every user of the informatics system can have a consultant status that is maintained by the system. The consultant status indicates whether or not the user is available for live consultations. The consultant status of each consultant may be managed by the informatics system based on one or more defined rules (e.g. user is currently logged in) or based on a user selection of an available status in their system user interface.

Figure 20:
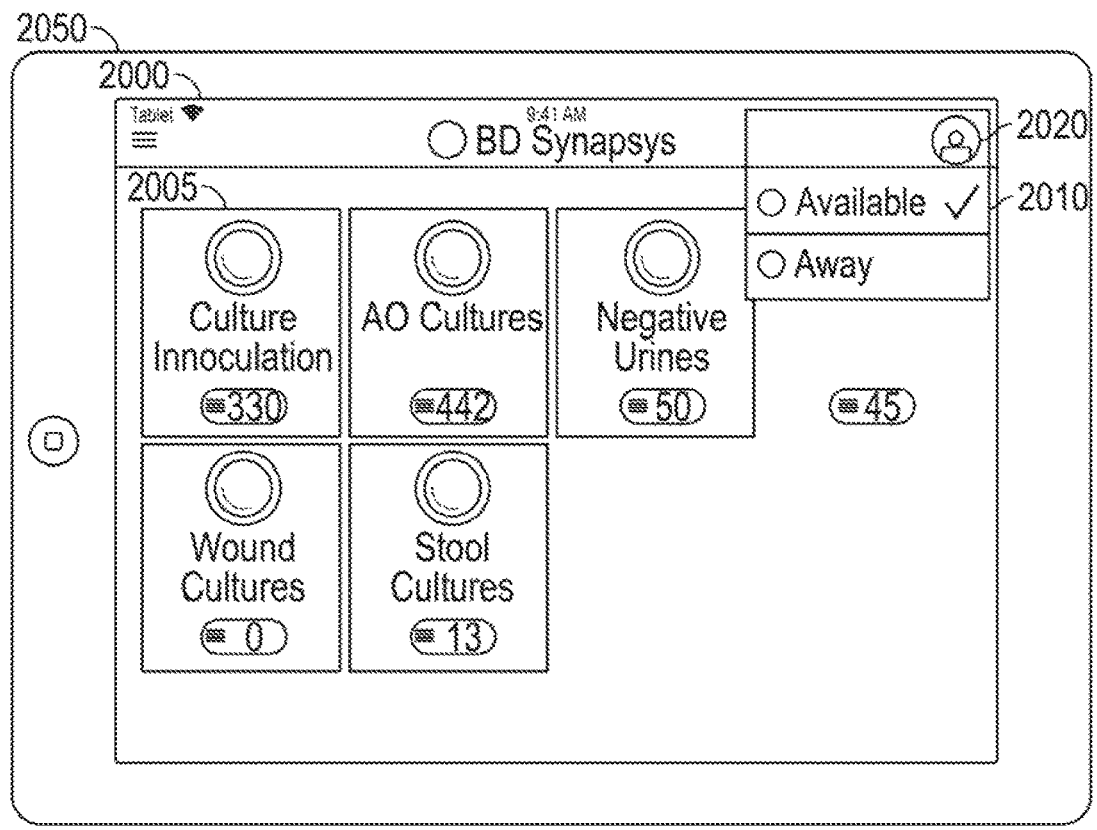
FIG. 20 depicts an example of a user interface display screen in accordance with an illustrative embodiment of the present invention.

FIG. 20 depicts an example of a user interface display screen 2000 of a device 2050 in accordance with an illustrative embodiment of the present invention. The device 2050 can include similar features and functions to those described with respect to the device 1800 as shown in FIG. 18. The display screen 2000 depicts a plurality of selectable culture plate image types 2005. Each culture plate image type 2005 may be selected to view one or more culture plate images associated with the culture plate image type 2005. The display screen 2000 further shows a selection of a consultant status 2010 of "Available" made by a system user 2020. Other selectable consultant statuses can include busy, not available, offline, etc.

Figure 21:
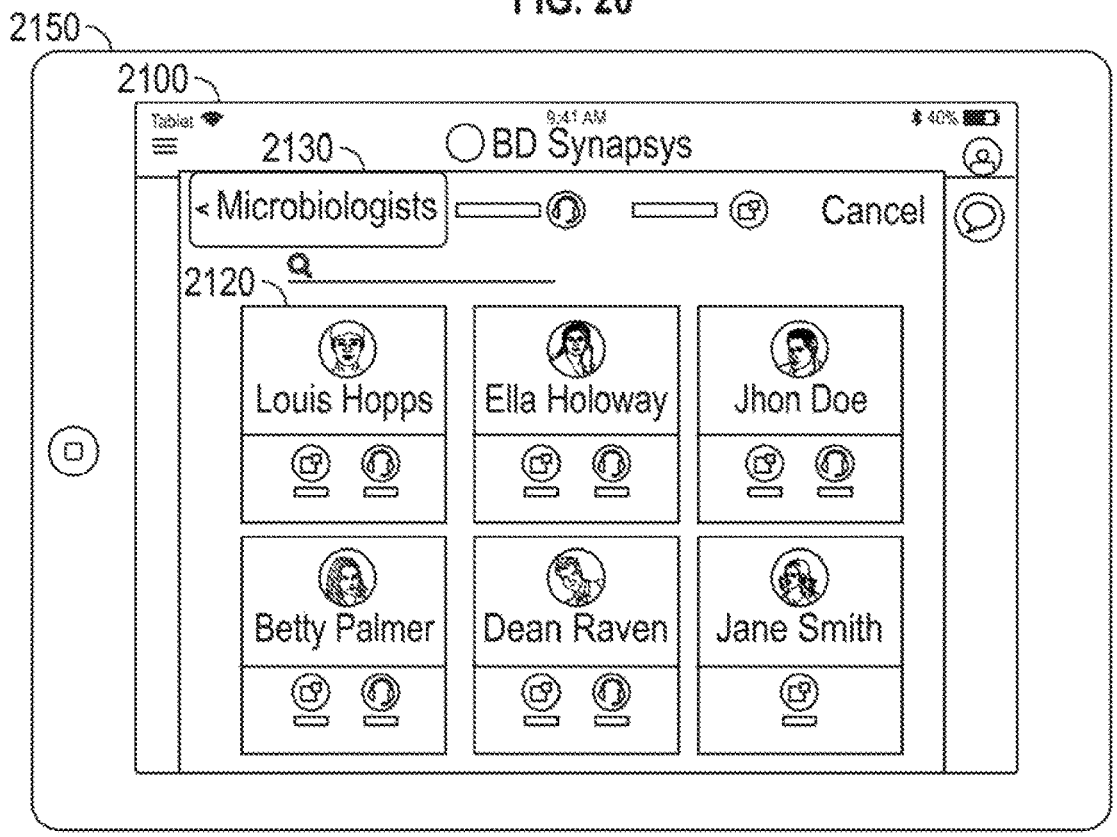
FIG. 21 depicts an example of a user interface display screen in accordance with an illustrative embodiment of the present invention.

A system user who can be consulted may be identified in the informatics system as part of one or more logical groups. For example, FIG. 21 depicts an example of a user interface display screen 2100 of a device 2150 in accordance with an illustrative embodiment of the present invention showing six users 2120 having been allocated to a logical group 2130. The device 2150 can include similar features and functions to those described with respect to the device 1800 as shown in FIG. 18. In FIG. 21, the logical group 2130 is a "Microbiologist" logical group. The informatics system may use the group 2130 to direct either live or deferred consultation requests to all available members 2120 of that group 2130.

In some embodiments, each user 2120 in the user group 2130 can select to respond to, accept, or deny a consultation request. In some embodiments, the informatics system can restrict the number of users within the user group 2120 that can respond to a consultation request. For example, in some embodiments, the informatics system may be configured to allow a first user 2120 who selects to respond to a consultation request to accept the consultation request and prevent any other users in the user group 2130 from accepting the request.

The functions and capabilities accessible to a user on the informatics system can be determined by the permissions the user has been assigned in the informatics system for consultation. For example, a consultant having restricted permissions for live consultation functionality may be able to view a shared display screen only, with access to limited annotation tools such as temporary visual marking or highlighting on the user interface that is not stored with the culture plate image. If a consultant has unrestricted permissions for live consultation, they may be able to view and control the technician's user interface display screen, enabling the consultant to perform functions and record data on the technician's behalf. A consultant with unrestricted permissions may also have full access to annotation tools.

If a consultant has restricted permissions for deferred consultation functionality, the consultant may be able to view culture data and images only, with access to commenting and annotation tools that may be stored with the culture, but may not be able to modify the culture data or images in any way. The consultant may not be able to perform system functions that result in lab instrument actions or communication of results to external systems. If the consultant has extended permissions for deferred consultation functionality, the consultant may be able to edit the culture data and images according to their permissions for the standard culture reading functionality in the system.

Live Consultation

When a technician requests a live consultation, for example, as described with respect to step 1950A of FIG. 19A, a consultant or consultant group will be notified of the request to establish a live consultation session. Each consultant can receive the notification on a device connected to the informatics system via a user interface. If an individual consultant is being requested, the individual consultant can decide whether or not to accept the consultation request by making a selection on their user interface. When a consultant group is sent a request, each individual consultant in the consultant group can receive a notification of the request. In some embodiments, each consultant in the group can accept or deny the request for a live consultation. In some embodiments, once one consultant or a defined number of consultants within a group have accepted the request for a live consultation, other consultants may be restricted from accepting the request for the live consultation. When the request for a live consultation is accepted, a communication channel can be established between the technician and the consultant. The communication can include one or more of audio, visual, and application user interface sharing.

Figure 22A:
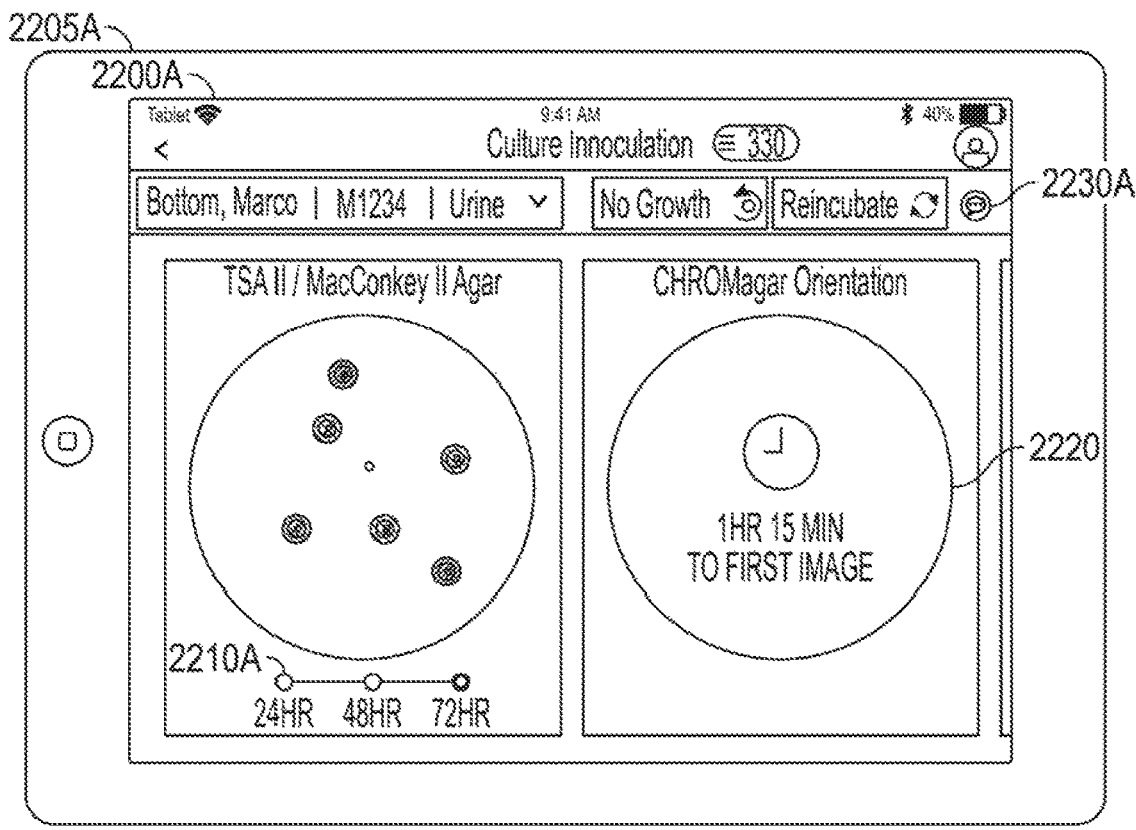
FIG. 22A depicts an example of a user interface display screen in accordance with an illustrative embodiment of the present invention.

FIG. 22A shows an example of user interface display screen 2200A of a device 2205A of a technician showing culture plate images. The device 2205A can include similar features and functions to those described with respect to the device 1800 as shown in FIG. 18. The display screen 2200A of FIG. 22A shows a timeline 2210A. The timeline 2210A can show a time at which a selected culture plate image is captured.

Figure 22B:
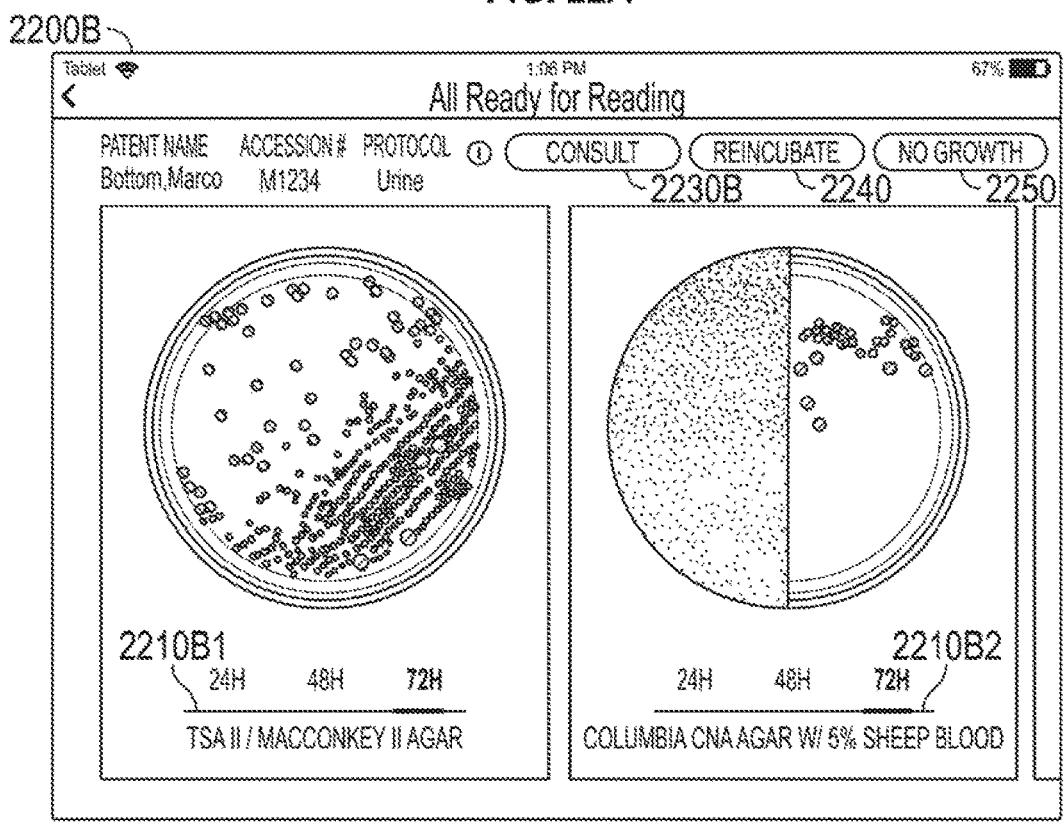
FIG. 22B depicts an example of a user interface display screen in accordance with an illustrative embodiment of the present invention.

The display screen 2200A further show a timer 2220 providing information regarding a time at which a new culture plate image will be captured. The display screen of FIG. 22A further shows a consultation initiation selection option 2230A in the upper right corner having a graphical indicia in the shape of a speech bubble. As shown in FIG. 22A, the selection option 2230A can be a selectable button. FIG. 22B shows an example of a user interface display screen 2200B of a technician. The display screen of FIG. 22B shows an alternative design wherein the consultation imitation selection option 2230B is labeled "consult" and appears next to a "REINCUBATE" option 2240 and a "NO GROWTH" option 2250. As shown in FIG. 22B, the options 2230B, 2240, and 2250 can be selectable buttons. The display screen 2200B shows a timeline 22101 and a timeline 2210B2.

To begin initiating a live consultation, a technician can select the consultation initiation selection option 2230A or 2230B. When initiating a live consultation, the technician may search for a preferred consultant group instead of a particular consultant. In some embodiments, a technician can select to see all active consultants, those that are logged into the system and have a status of available for consultation. Selecting a consultant group for live consultation can cause the informatics system to attempt to initiate a consultation session with all active members of that group. In one embodiment of the system, after a connection is established with one consultant of the consultant group, the system will stop efforts to connect with other active consultants in the group. In another embodiment, the informatics system will continue to attempt to establish calls with other active consultants in the group for a configurable amount of time or until the active consultant declines the call.

Figure 23:
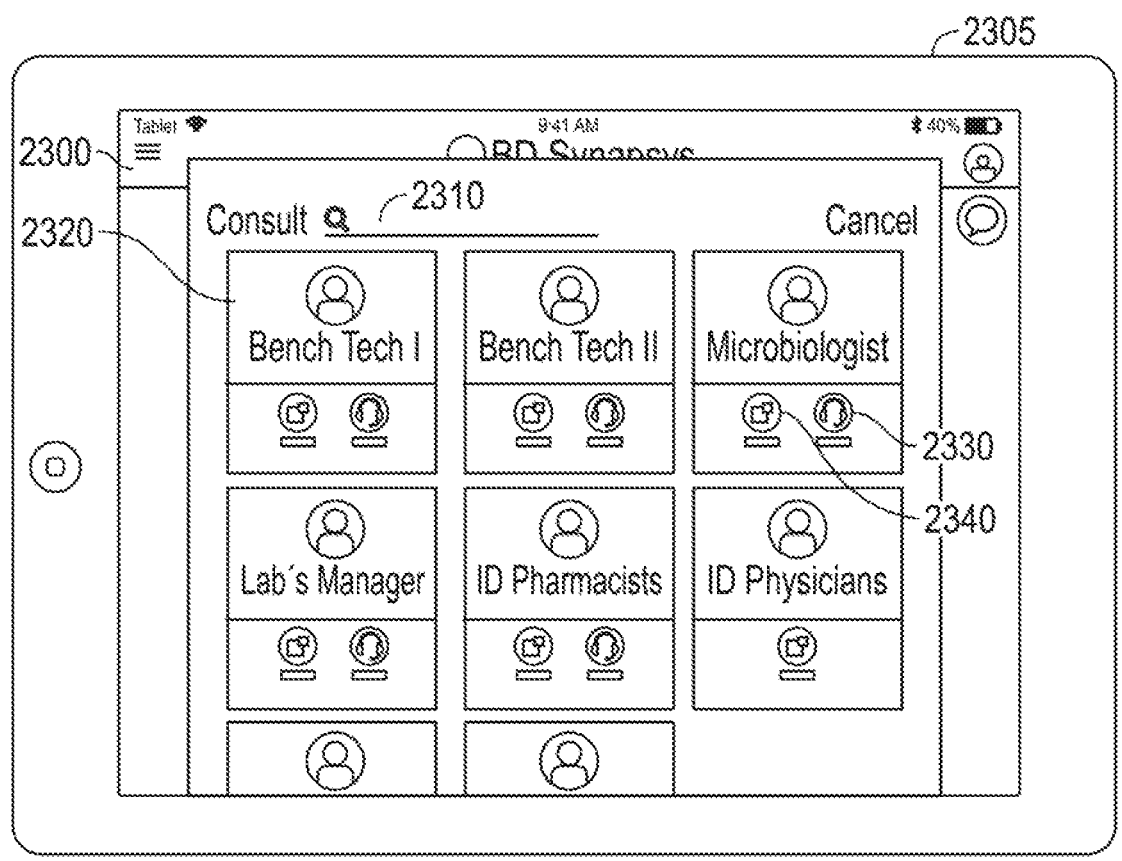
FIG. 23 depicts an example of a user interface display screen in accordance with an illustrative embodiment of the present invention.

FIG. 23 depicts an example of a user interface display screen 2300 of a device 2305 in accordance with an illustrative embodiment of the present invention. The device 2305 can include similar features and functions to those described with respect to the device 1800 as shown in FIG. 18. The display screen 2300 is a consultant request screen having a consultant search bar 2310 to allow for the input of a name of a consultant or consultant group for searching within the informatics system. As shown in FIG. 23, consultant groups 2320 can be listed along with contact options for the consultant group. For example, there may be separate selectable options for a live or delayed consultation. FIG. 23 shows an option 2330 for selecting a live consultation for a "Microbiologists" consultant group 2320. As shown in FIG. 23, the option 2330 can be a selectable button. The option 2330 for selecting a live consultation with a consultant group or individual consultant may not be available for selection in the user interface, when the informatics system determines the consultant or all members of a consultant group, are of a status unavailable for live consultation. The screen 2300 further shows an option 2340 for selecting a delayed consultation for the "Microbiologists" consultant group 2320. As shown in FIG. 23, the option 2340 can be a selectable button.

Figure 24:
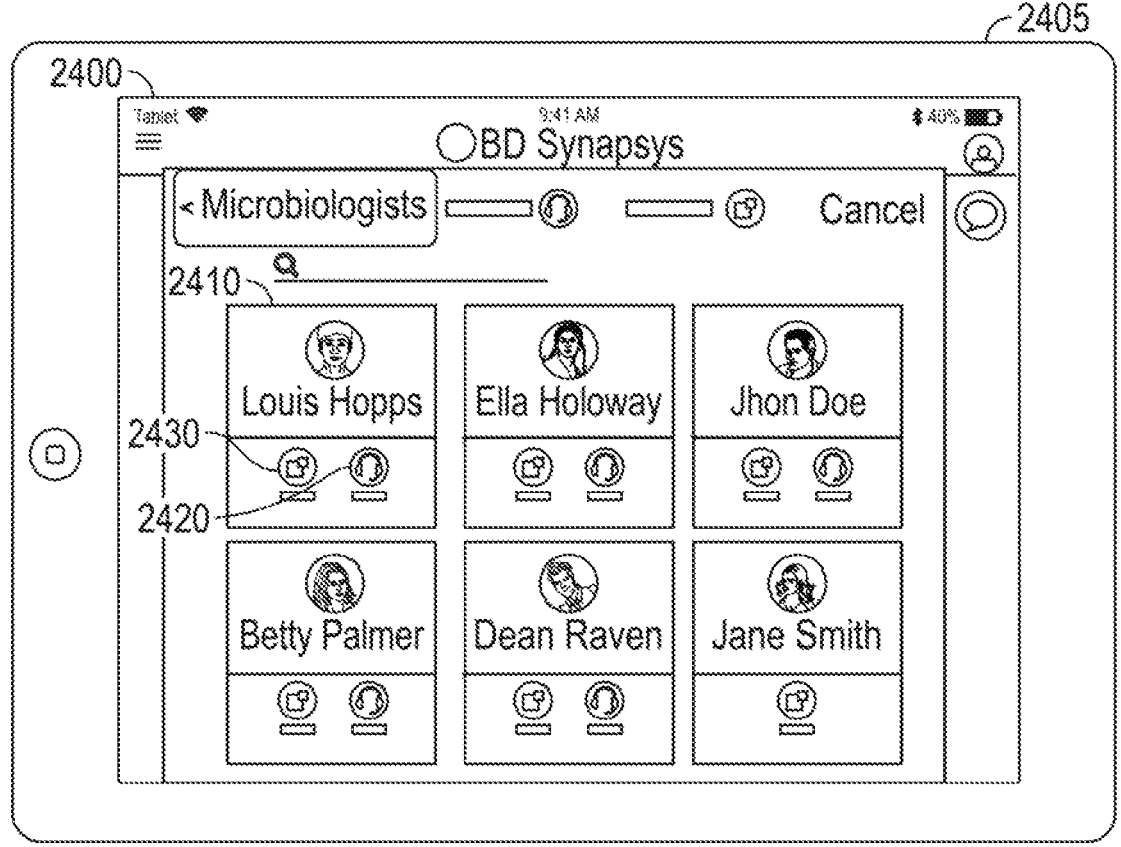
FIG. 24 depicts an example of a user interface display screen in accordance with an illustrative embodiment of the present invention.

FIG. 24 depicts an example of a user interface display screen 2400 of a device 2405 showing a set of consultants 2410 of the "Microbiologists" consultant group 2320 of FIG. 23. The device 2405 can include similar features and functions to those described with respect to the device 1800 as shown in FIG. 18. In some embodiments, the display screen 2400 can be accessed by a selection of the "Microbiologists" consultant group 2320 using the display screen 2300. A selectable option 2420 can be associated with each consultant 2410 that can be selected to initiate a live consultation with the selected consultant 2410. A selectable option 2430 can be associated with each consultant 2410 that can be selected to initiate a delayed consultation with the selected consultant 2410. As shown in FIG. 24, the options 2420 and 2430 can be selectable buttons.

When a live consultation is initiated, the selected consultant will be notified with visual and audible cues that a live consultation has been requested. As shown in FIG. 24, selecting a consultant group can display the active members of that group, allowing the technician to initiate a consultation session with a specific member of that group. To begin the consultation, the consultant(s) must accept the consultation request.

Figure 25:
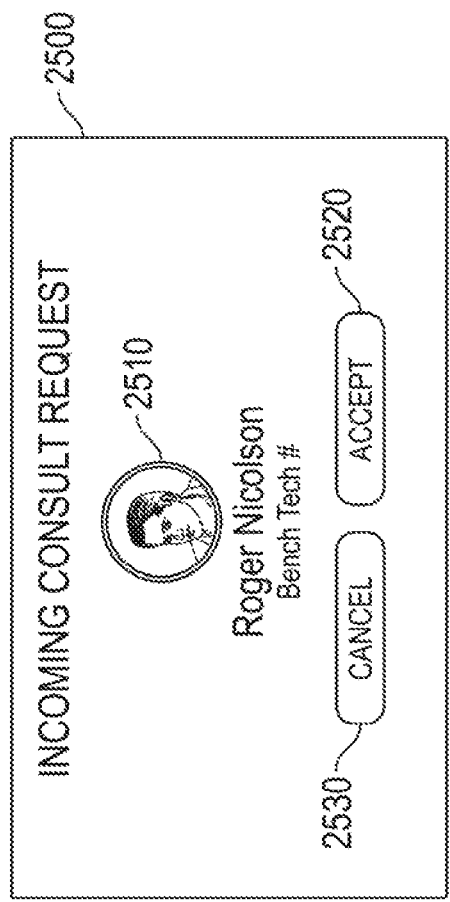
FIG. 25 depicts an example of a user interface display screen in accordance with an illustrative embodiment of the present invention.

FIG. 25 shows an example of a user interface display screen 2500 that can be presented to a consultant on a device of the consultant, such as the device 1800 as shown in FIG. 18, when a technician requests a consultation with the consultant. The display screen 2500 can include a user identification icon 2510 identifying the technician requesting consultation. The display screen 2500 can also include a selectable option 2520 that can be selected for accepting the consultation request and a selectable option 2530 for cancelling or declining the consultation request. As shown in FIG. 25, the options 2520 and 2530 can be selectable buttons. The consultant can select to accept or cancel the consultation request using selectable options 2520 and 2530 on their user interface display screen 2500. If accepted, the live consultation established allows for concurrent collaboration between the parties, according to the permissions they have in the system, as described herein.

In some embodiments, when a live communication is in progress, the technician and consultant can interact with existing software functionality for viewing and manipulating digital images and navigation within the relevant software functionality according to that consultant's user permissions within the system. In some embodiments, user interface actions performed by one party to the consultation can be visible to the other user. The informatics system can provide user interface tools, which may be available to both the technician and the consultant, to visualize, highlight, and draw attention to locations on the culture plate image or other parts of the user interface. In some embodiments, the tools can be similar to the selection tools described above with respect to FIGS. 1-17. In some embodiments, the user interface tools can allow the users to visualize, highlight, and draw attention to locations on the culture plate image or other parts of the user interface without modifying the culture plate image or effecting system functionality. Audio and video communications may be established to assist in the collaborative communication through a communication channel. A communication channel can allow communication using wired or wireless communication, cell communication, Bluetooth®, ZigBee®, LAN, WLAN, RF, IR, or any other communication method or system known in the art. Audio communications may be recorded by an internal microphone on the device which the user is using to connect to the informatics system or on an external microphone. In some embodiments, the device can include a speaker for emitting audio communications. Video communication may be recorded using a camera on the device through which the user is connecting to the informatics system or an external camera. Video recordings of the user interface display screen of a technician or consultant can be recorded and/or transmitted by software of the device on which the particular consultant or technician is accessing the informatics system.

In some embodiments, either user may terminate a consultation session via a selection on their user interface. When a user terminates a consultation session, their user interface may return to the prior state or workflow activity present on the user interface before the consultation session was established.

Figure 26:
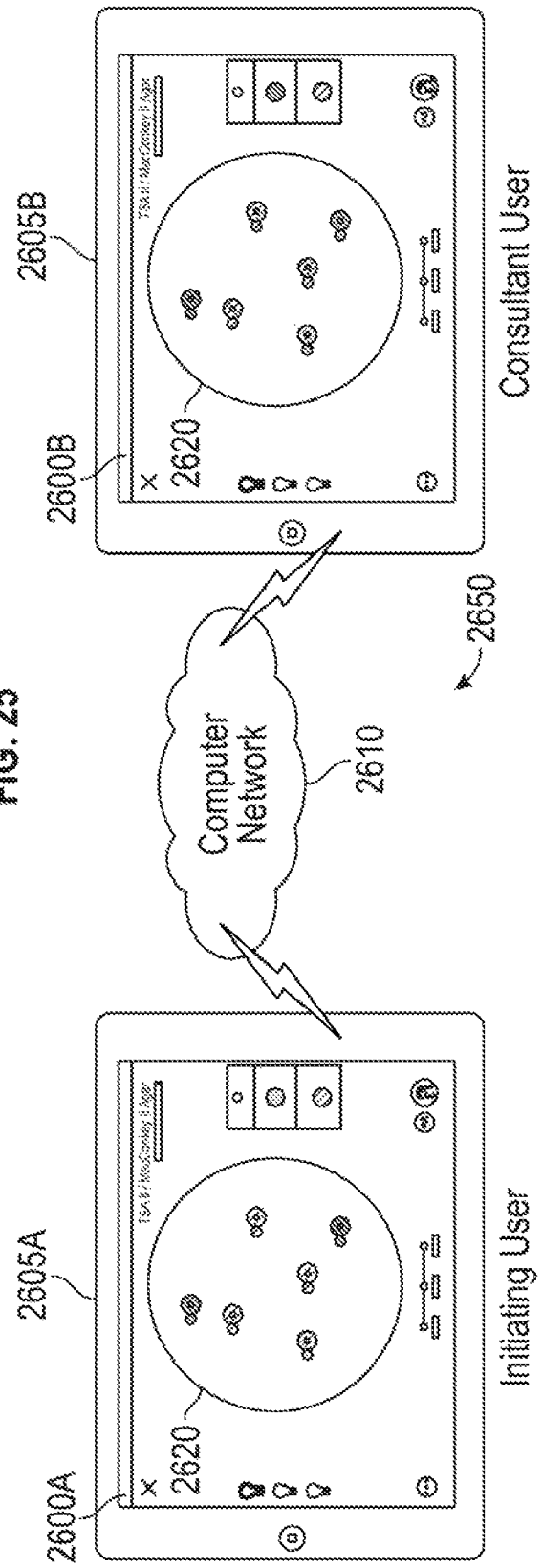
FIG. 26 depicts an example of a consultation system in accordance with an illustrative embodiment of the present invention.

FIG. 26 depicts a consultation system 2650 showing an example of the user interface display screen 2600A of a device 2605A of a technician during a live consultation and the user interface display screen 2600B of a device 2605B of a consultant during the live consultation. The devices 2605A and 2605B can include similar features and functions to those described with respect to the device 1800 as shown in FIG. 18. The devices 2605A and 2605B can be in communication over a computer network 2610. As described herein, the informatics system can allow for the display of a shared culture plate image during a live consultation. As shown in FIG. 26, the user interface display screen for each party shows the same culture plate image 2620.

Figure 27:
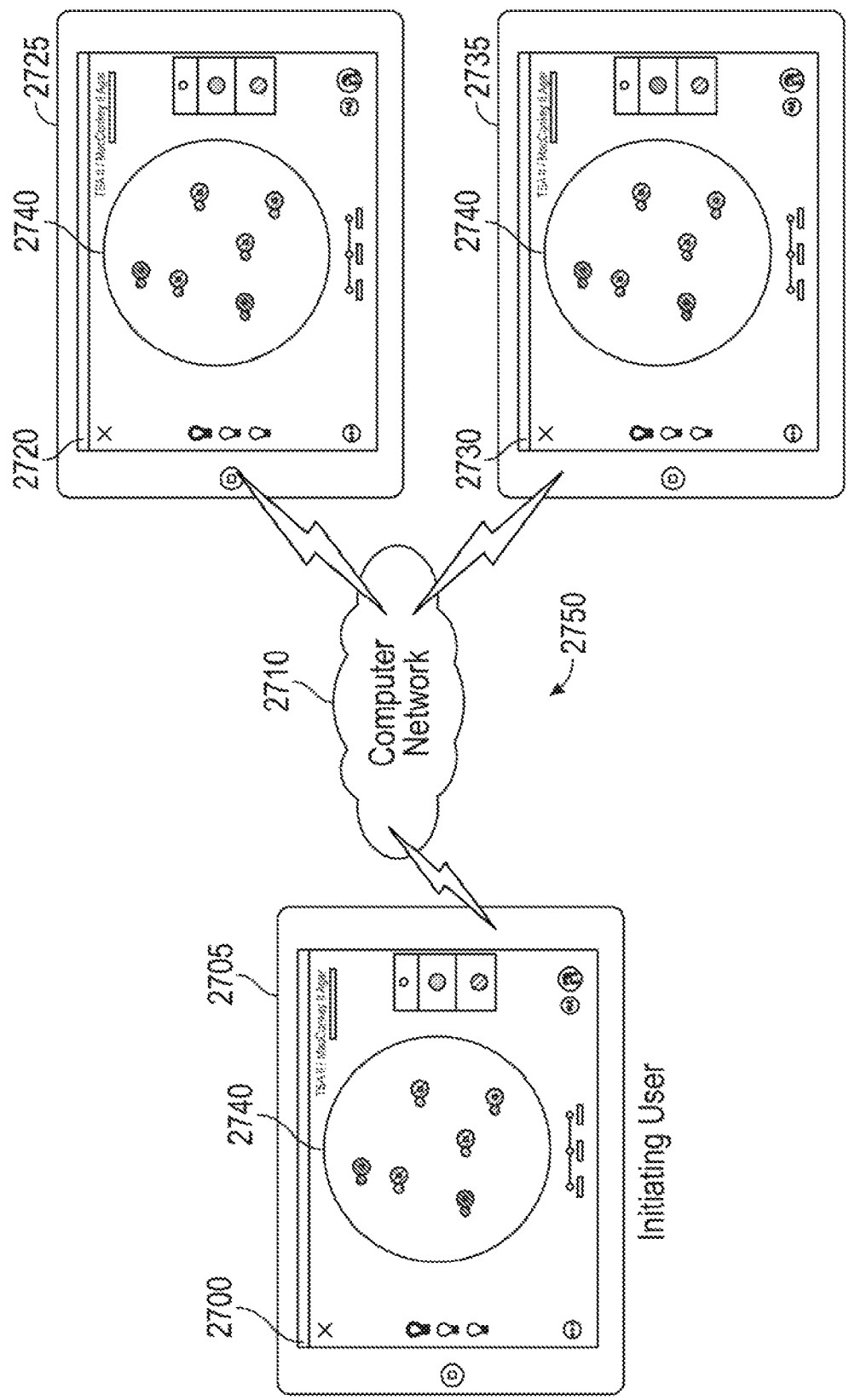
FIG. 27 depicts an example of a consultation system in accordance with an illustrative embodiment of the present invention.

FIG. 27 depicts a consultation system 2750 showing an example of a consultation in which a technician is consulting with two consultants. This can occur when a technician chooses to send consultation request to multiple consultants, when a technician sends a consultation request to a consultation group and multiple consultants respond, or by adding additional consultants during the consultation. FIG. 27 shows a user interface display screen 2700 of a device 2705 of a technician in communication over a network 2710 with a first consultant operating a user interface display screen 2720 of a device 2725 and a second consultant operating a user interface display screen 2730 of a device 2735. The devices 2705, 2725, and 2735 can include similar features and functions to those described with respect to the device 1800 as shown in FIG. 18. Each of the display screens 2700, 2720, and 2730 can share a culture plate image 2740. Additional consultants can be added to an existing live consultation session by repeating steps described herein for consulting an individual consultant. The live consultation session can be terminated by any party. If the session is terminated by the technician, the session can be terminated for all connected consultants. If multiple consultants are part of a live consultation session, and a consultant terminates the call, the informatics system can be configured to only disconnect the terminating consultant from the live consultation session. If only one consultant remains in the live consultation session, and they terminate the call, the informatics system can be configured to terminate the consultation session.

Figure 28:
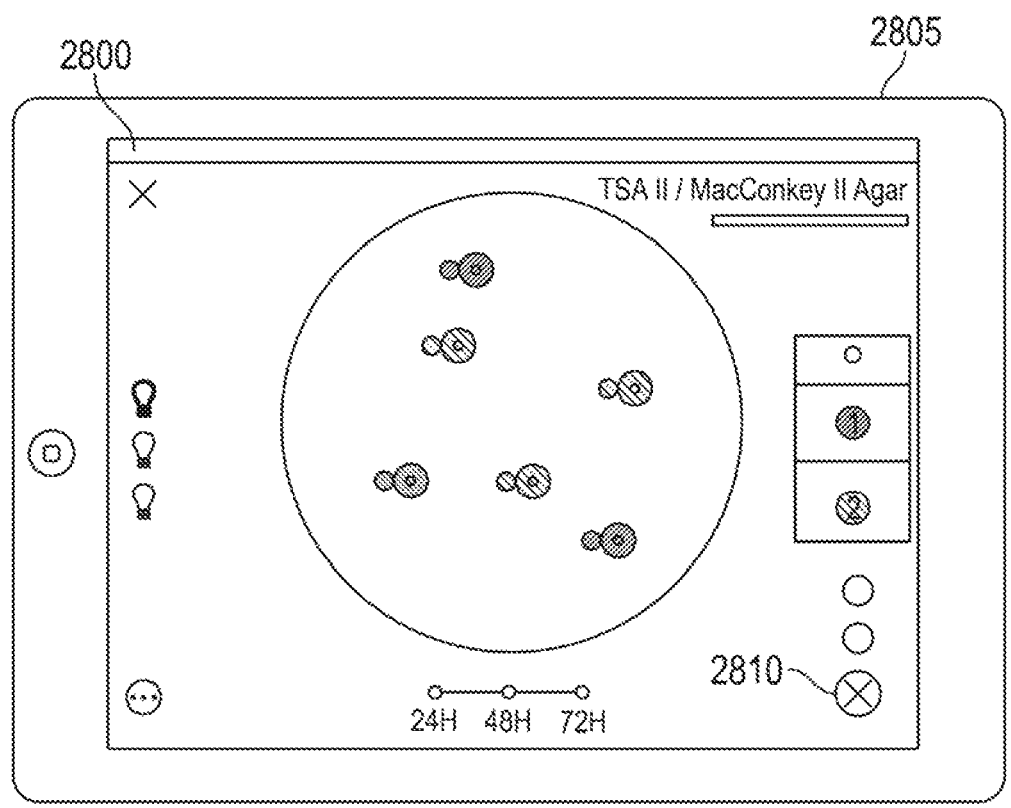
FIG. 28 depicts an example of a user interface display screen in accordance with an illustrative embodiment of the present invention.

FIG. 28 shows an example of a user interface display screen 2800 of a device 2805 during a consultation session. The device 2805 can include similar features and functions to those described with respect to the device 1800 as shown in FIG. 18. The display screen 2800 includes a selectable option 2810 for terminating the consultation session.

When in a live consultation session, critical elements of data visible in the technician's application user interface can be displayed concurrently on the user interface of the consultant(s). This concurrent display of data between the consulting parties may take multiple forms, to account for the variations in device form factors, operating systems, and native application displays in use between the different users. The concurrent display of data may include sharing of the full user interface display screen visible on the technician's system which may occur when the form factors and application technologies are the same between technician and consultant(s).

Figure 29:
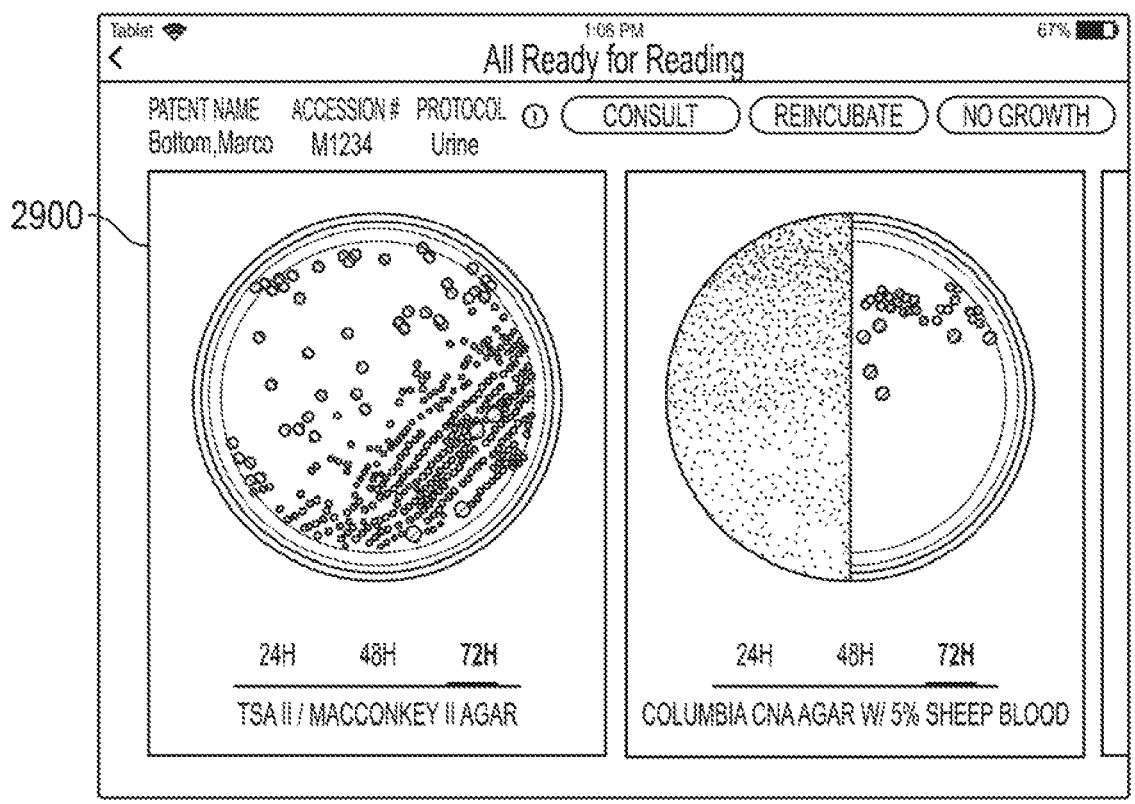
FIG. 29 depicts an example of two user interface display screens in accordance with an illustrative embodiment of the present invention.
Figure 29:
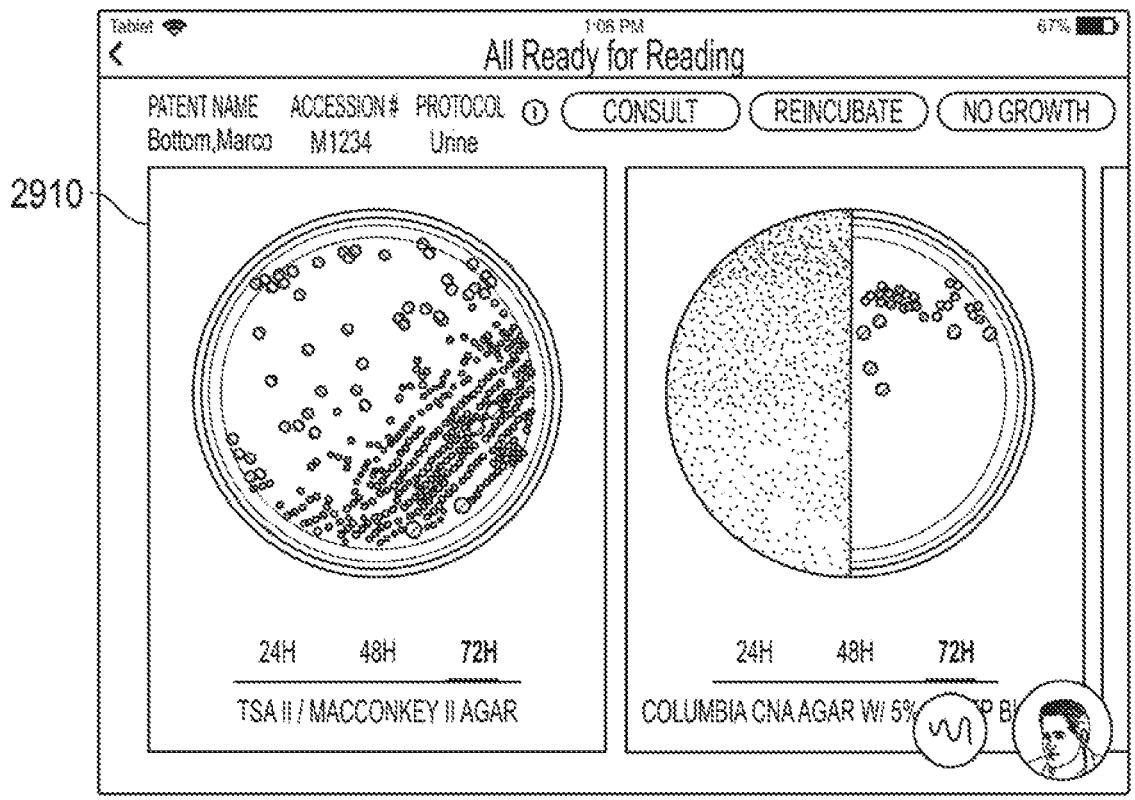

FIG. 29 shows an example of a user interface display screen 2900 of a technician and a user interface display screen 2910 of a consultant in which the full user interface display screen 2900 of the technician is visible to the consultant on the display screen 2910. The user interface display screen 2900 of the technician and the user interface display screen 2910 of the consultant can each be operated on devices, such as the device 1800 as shown in FIG. 18. In some embodiments, particular data elements or images may be shared by the user to the consultant, without providing the full user interface display screen of the technician to the consultant. This may occur when the form factors and application technologies differ between devices used by the technician and consultant(s) to access the informatics systems. This can also occur based on different permissions provided to technician(s) and consultant(s) in the informatics system.

Figure 30:
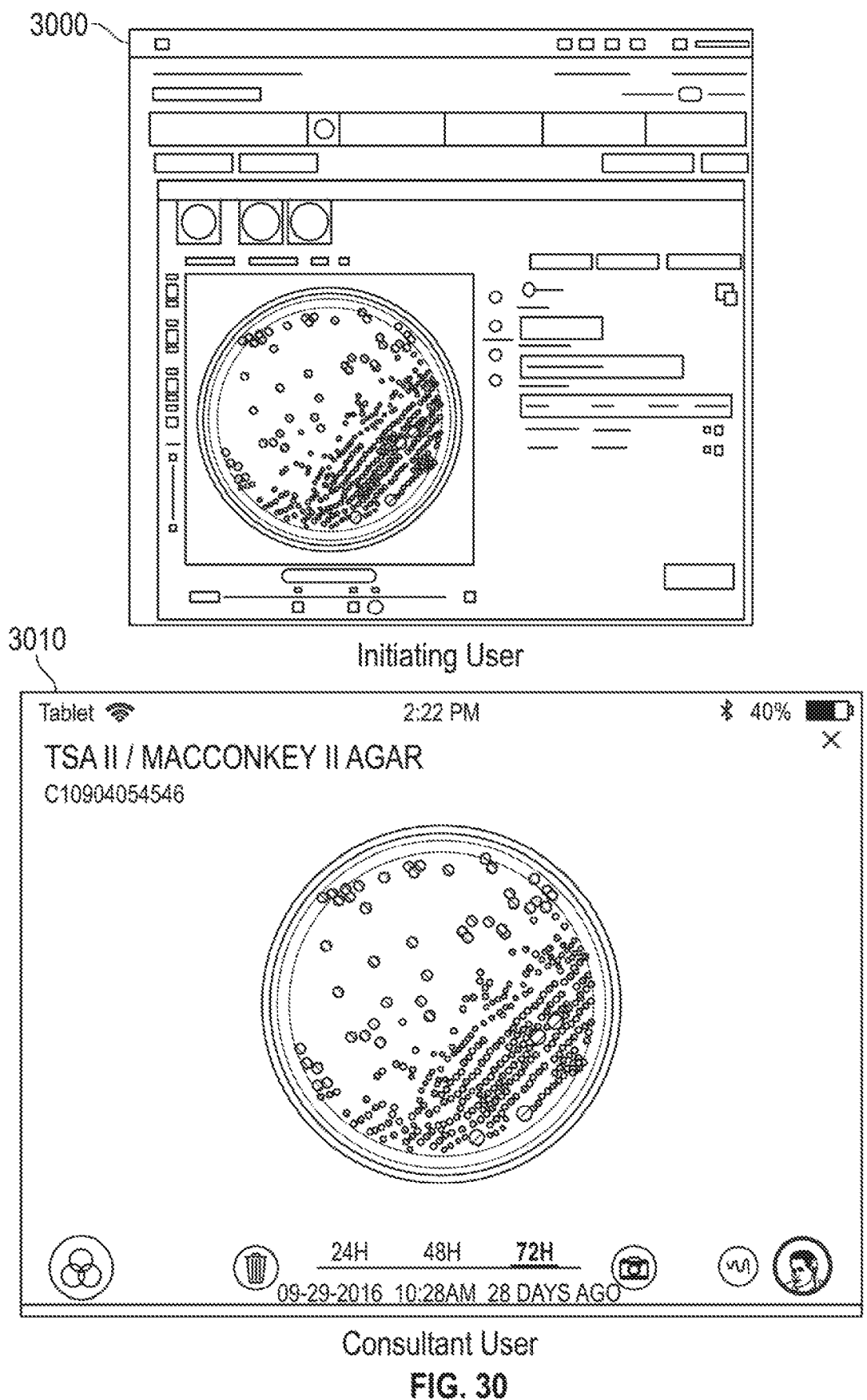
FIG. 30 depicts an example of two user interface display screens in accordance with an illustrative embodiment of the present invention.

FIG. 30 shows an example of the user interface display screen 3000 of a technician and a user interface display screen 3010 of a consultant in which only some data elements of the user interface display screen 3000 are visible to the consultant on the display screen 3010. The user interface display screen 3000 of the technician and the user interface display screen 3010 of the consultant can each be operated on devices, such as the device 1800 as shown in FIG. 18.

Figure 31:
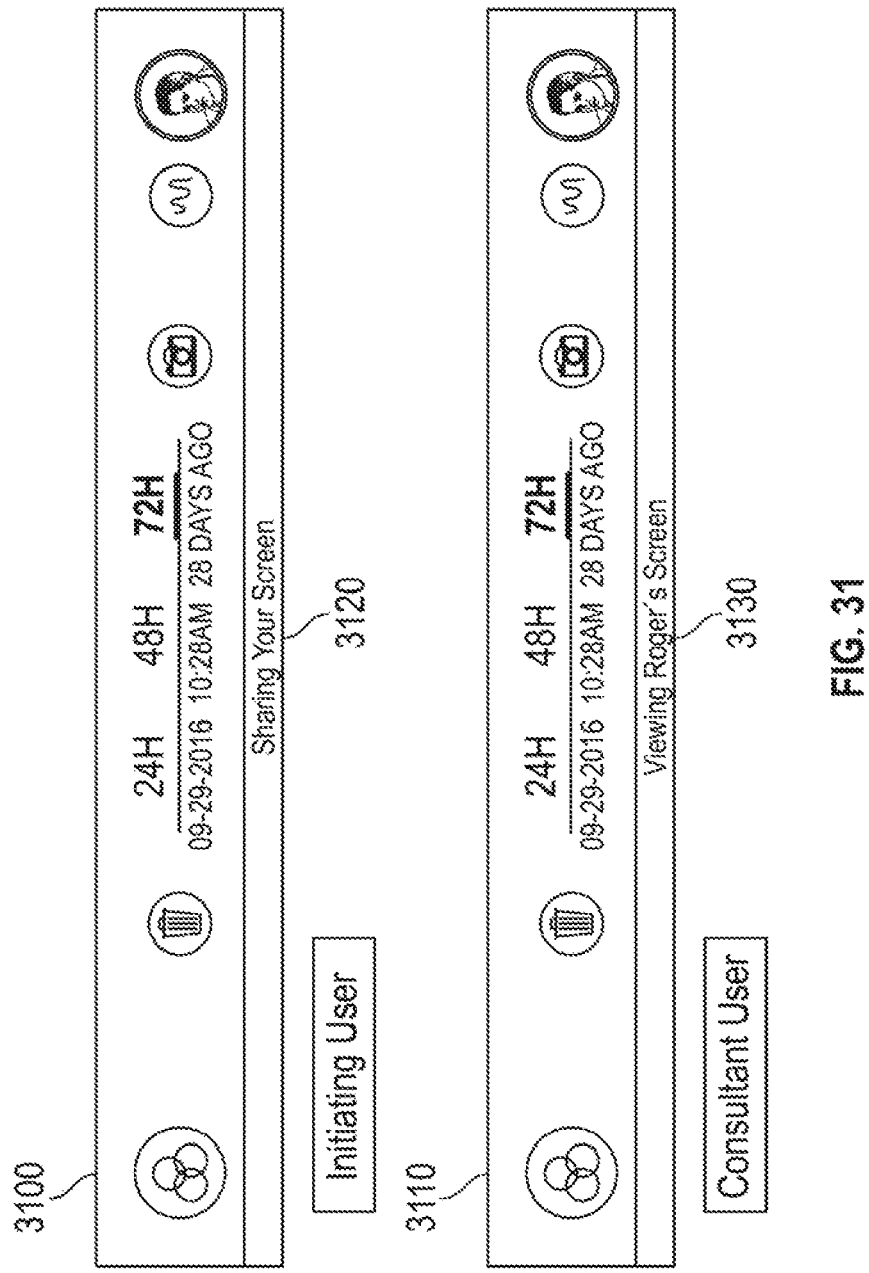
FIG. 31 depicts an example of sections of two user interface display screens in accordance with an illustrative embodiment of the present invention.

When in a live consultation session, the system may indicate on the technician and consultant screens that a session is in progress. The system may indicate the parties involved in the call and provide system controls to manage the session. For example, FIG. 31 shows an example of a section of a user interface display screen 3100 of a technician and a section of a user interface display screen 3110 of a consultant in which the display screen 3100 includes an indicator 3120 that the technician is sharing the display screen 3100. The display screen 3110 can also include an indicator 3130 that indicates that the consultant is viewing the display screen 3100 of the technician on the display screen 3110.

In a live consultation session, the informatics system can enable audio communication between all the parties. The parties can also establish a video sharing communication enabling the parties to see each other in addition to screen sharing.

In some embodiments, an indicator tool can be provided to one or more of the technician and the consultant. An indicator tool can be a visible icon that can appear on a shared user interface display screen and can be manipulated by the technician and/or consultant using an input. In some embodiments, the indicator tool will become visible to all users when activated by any user involved in the consultation session (for example by mouse click or touch screen interaction). The indicator tool can be identifiable as belonging to a particular system user. The indicator tool may take a variety of forms, including that of an icon representing a pointer or target reticle, a shaped highlight area, or a magnified area of the user interface under selection. The indicator tool may also take a similar form to the selection tools described herein with reference to FIGS. 1-17.

Figure 32:
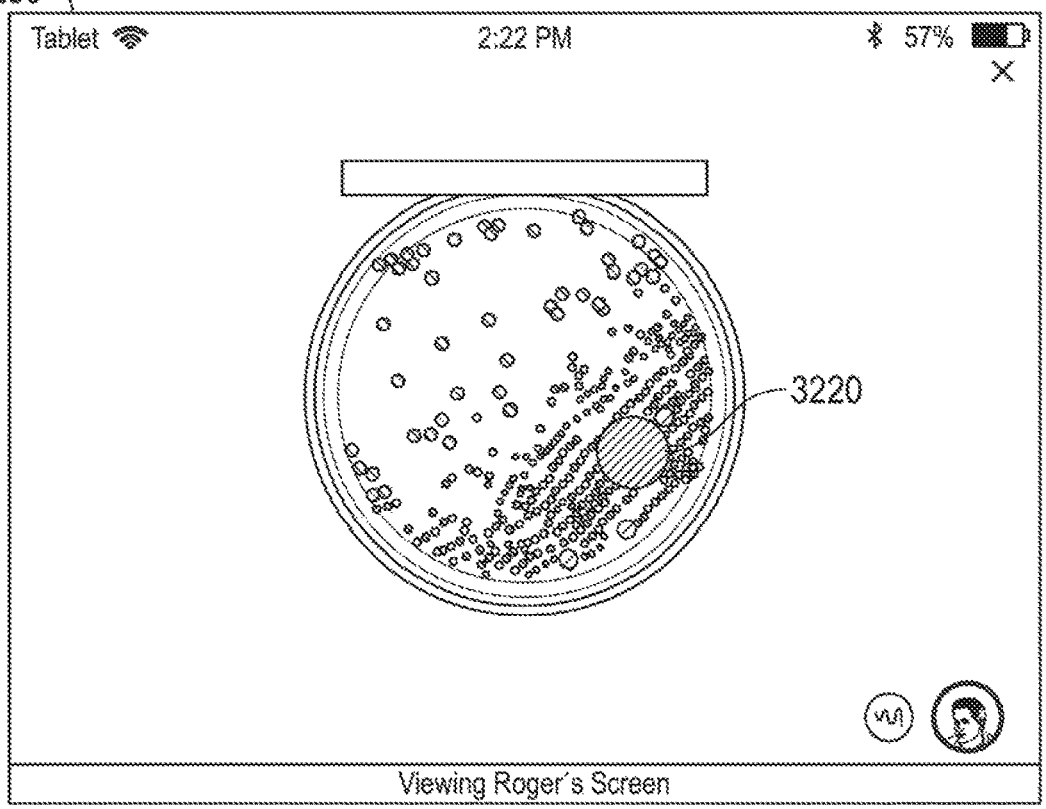
FIG. 32 depicts an example of two user interface display screens in accordance with an illustrative embodiment of the present invention.
Figure 32:
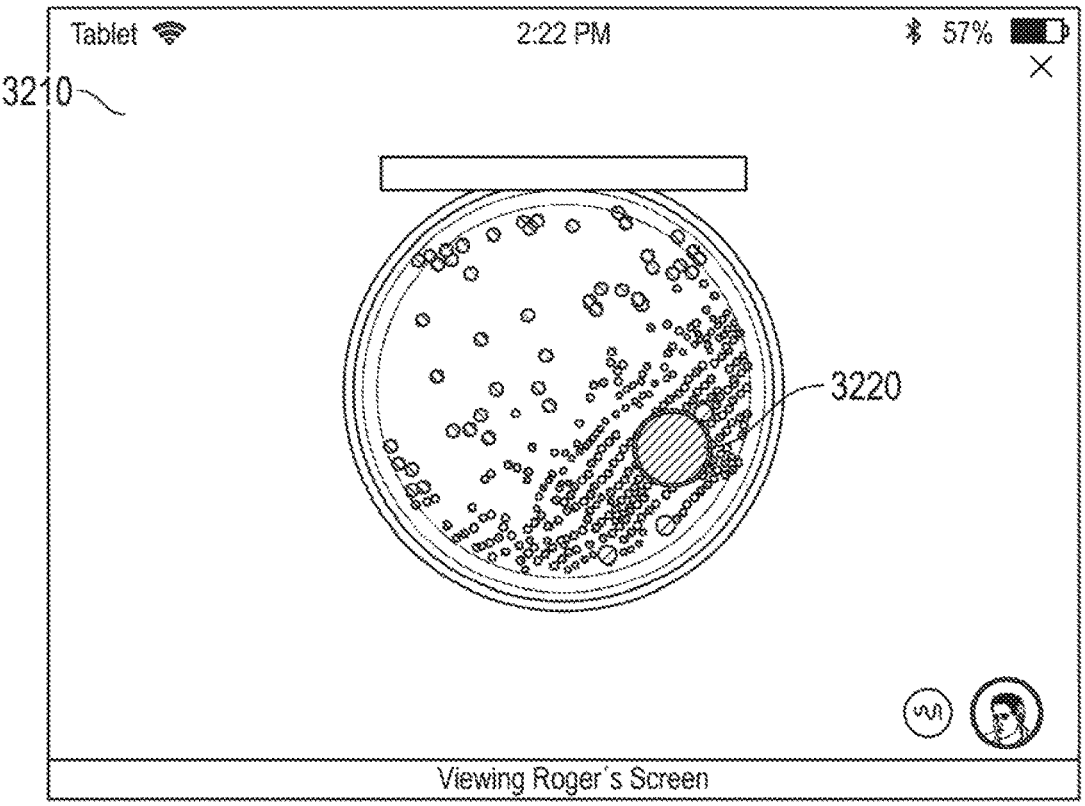

FIG. 32 shows an example of an indicator tool 3220 appearing on a user interface display screen 3200 of a technician and a user interface display screen 3210 of a consultant. The user interface display screen 3200 of the technician and the user interface display screen 3210 of the consultant can each be operated on devices, such as the device 1800 as shown in FIG. 18. In FIG. 32, the user interface display screen 3200 is shared with the consultant on the display screen 3210. The indicator tool 3220 is in the shape of a circle and can be moved across the shared user interface display screen by the technician and/or the consultant.

To assist the consultation session, an image annotation tool can also be available for one or more users during the live consultation session. The image annotation tool can allow a user involved in the collaborative session to draw a temporary free-style line on the user interface or culture plate image. In one embodiment, the drawn annotation remains visible on all screens until explicitly cleared by any user involved in the collaboration session. In another embodiment, the drawn annotations are visible for a definable period of time, after which they are automatically removed from all user interfaces.

Figure 33:
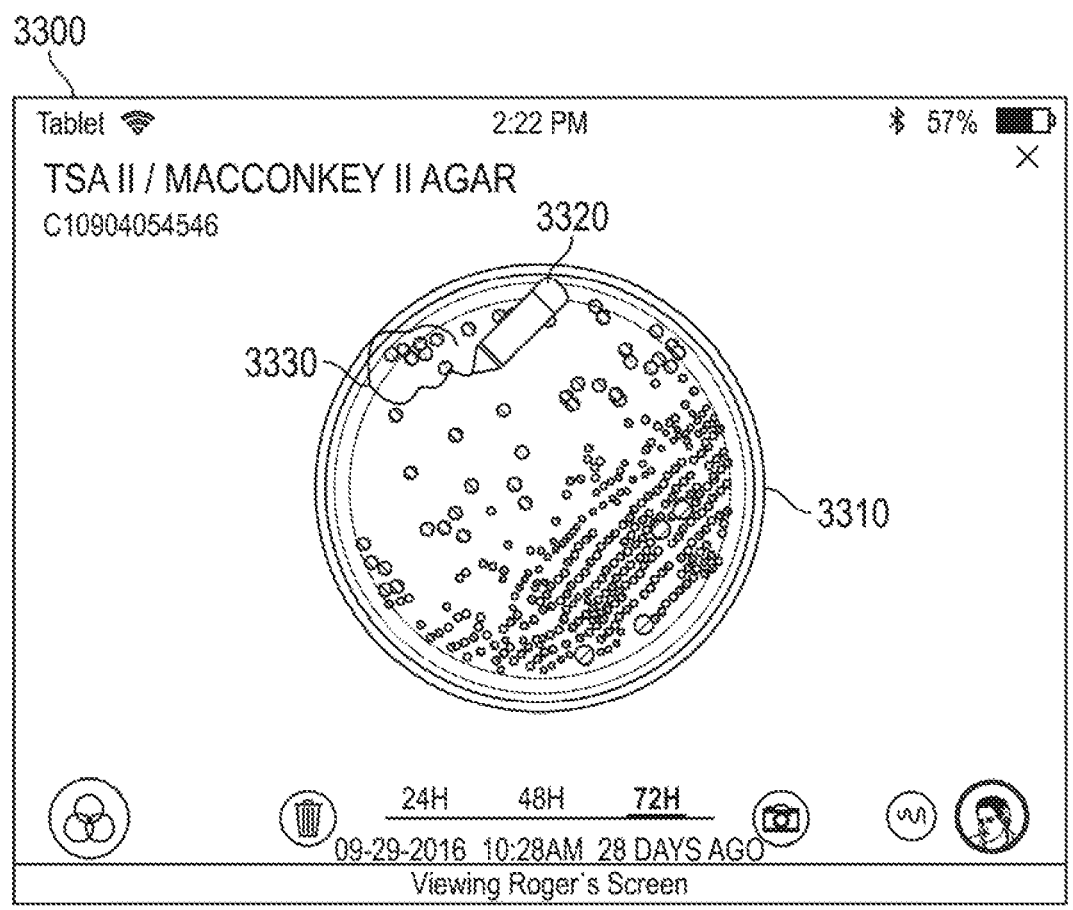
FIG. 33 depicts an example of a user interface display screen in accordance with an illustrative embodiment of the present invention.

FIG. 33 depicts an embodiment of a user interface display screen 3300 showing a culture plate image 3310 and an image annotation tool 3320. The user interface display screen 3300 can be operated on a device, such as the device 1800 as shown in FIG. 18. The image annotation tool 3320 is shaped to look like a writing instrument. When using the image annotation tool 3320, a technician or consultant can select when to cause the image annotation tool to draw on the user interface display screen, for example, by clicking and holding a button on an input, such as input 1830 as shown in FIG. 1800. In some embodiments, the input is a mouse. The user interface display screen 3300 also shows an example of an annotation 3330 created using the annotation tool 3320.

Deferred Consultation

As described herein, with respect to FIG. 19B, when a lab technician requires assistance in making decisions on the disposition of a culture, they may initiate a deferred consultation request to another consultant or consultant group, by selecting an appropriate software control on the user interface. The deferred consultation option enables tools for documenting the request or question in text or recorded digital formats. Digital formats may include recording of screen interaction paired with audio recording of the technician. The deferred consultation option further enables tools for selecting the digital images for consideration, tools to visually highlight or otherwise annotate segments of the user interface display screen of the user, such as annotation tool 3320, without modifying the digital images or culture data so that an annotated copy of the display screen or portion thereof can be sent with the consultation request, worklist and user notification capabilities to organize consultation requests and indicate when consultation requests are initiated or completed, and tools for a consultant to document a response to the consultation request.

The consultation request may include text comments, culture plate images, user interface display screen images, such as the images shown on the user interface display screens of FIGS. 22A, 22B, and 26-33, visual annotations to highlight locations on a culture plate image without modifying the images or effecting system functionality, such as annotation 3330 in FIG. 33, and recorded audio or visual commentary intended for the consultant. The consultant can be notified of the request via their respective system user interface, and access consultation request information and the data shared by the technician for review.

When the consultant reviews the deferred consultation request, the consultant can view textual comments, visual annotations and recorded audio or visual commentary provided by the technician. In some embodiments, the consultant is able to use the same tools and functionality for making visual annotations and commentary back to the technician. In some embodiments, the consultant is able to conclude the deferred consultation by setting a workflow state, such as "done", "inconclusive", "needs further analysis," etc. The workflow state applied to the culture can determine if the culture is concluded, or will appear on a worklist for the initiating technician or another lab technician to conclude reading and interpretation activities.

As an example, with reference to FIG. 22A, in some embodiments, the initiation selection option 2230A can be a deferred consultation initiation selection button. To begin initiating a deferred consultation, a technician can select the deferred consultation initiation selection button 2230A.

As with a live consultation, a technician may search for their preferred consultant group. For example, as described with respect to FIG. 23, the consultant request screen 2310 can include a consultant search bar 2310 to allow for the input of a name of a consultant or consultant group for searching within the informatics system. As described with respect to FIG. 23, there may be separate selectable options for a live or deferred consultation, an option 2330 for selecting a live consultation and an option 2340 for selecting a deferred consultation.

The user interface of the technician of the deferred consultation request can provide tools available for selecting the relevant data elements and digital images to be considered/shared with the consultant for the consultation and tools to record the details of the consultation request as discussed herein.

After a technician creates a deferred consultation request, consultants of the informatics system who are members of a consultant group selected for the deferred consultation will be notified of a pending consultation request and can access a worklist of pending consultations via a navigation option.

In one embodiment, consultants who are members of selected consultant group can be actively notified of pending consultation requests while they are logged in to the informatics system. Any consultants not logged in at the time of the request can be notified of the pending request at the time at which they log into the system. In another embodiment, consultants who are members of the selected consultation group will not be sent a notification, but can determine they have pending consultation requests by navigating to a worklist indicating pending request activity.

A consultant in the selected consultant group can select a consultation request from the pending consultation worklist. After selecting the consultation request, the consultant can be presented with the data, images and the consultation request provided by the technician. The consultant can provide a response to the consultation request using the tools described herein and according to the permissions they have in the system.

The deferred consultation session can be completed when the consultant completes one or more tasks provided by the technician in the consultation request, when the consultant selects to terminate the consultation, or when the consultant indicates that further steps need to be performed by a different actor. For example, a deferred consultation session can be completed when the consultant completes the reading and interpretation of a culture or when the consultant indicates that the culture should be returned to the lab for further workup according to their instructions.

In one embodiment a returned culture with an indication from the consultant that further processing is required may be made available to any lab technician for completion. The currently logged in user responsible for culture reading, which may be the technician, may receive a notification that a deferred consultation has been completed.

In another embodiment a returned culture may be made available to only the initiating technician for completion. The initiating technician may receive a notification that a deferred consultation which they requested has been completed.

One or more of the users of deferred consultation will have the ability to record text comments explaining the nature of the consultation request or the response to consultation request. Within the text comments, the user may include hyperlinks references to specific culture plates, digital images or image annotations described below. Text comments can be identified by meta-data that identifies the user and time of comments.

In another embodiment, a user may elect to document the nature of the consultation request using an audio/visual recording. The user can initiate a recording of all screen activity and audio, navigating through the application while narrating a question or answer. When recording is stopped, the recording can be attached to the consultation request or consultation request response.

For a particular culture, many images across multiple media may be available for review. The technician may elect to make only a subset of these digital images available to the consultant. The technician may select specific culture media for sharing, making all images associated to that culture plate available for review (including all images in time series and across different light source variations). The technician can also select one or more specific image(s) on a media, making other images related to the culture media unavailable for review.

Where a technician has elected to share a specific image, all consultants may have the ability to provide digital markings on the image to focus attention to a specific area of the digital image, for example, with an annotation tool such as described with respect to FIG. 33. Each digital marking made on an image can have its own meta-data for differentiation (such as marking number, title and comments). The digital markings can be visible to the consultant or technician when they receive the consultation request or consultation response. Alternatively, the digital markings can be hidden from the image so as not to obscure the image and can be toggled on and off by a selection of the technician or consultant. In some embodiments, a notification is provided that an image has digital markings that are not currently shown. Embodiments of digital markings can include iconographic markers indicating a specific image coordinate, a highlighted area on an image, a freeform shape drawn on the image, or any other digital markers as described herein. Digital markings can be made on a culture plate image or on other sections of a user interface display screen containing the culture plate image. While systems and methods for consulting on culture plate readings are described, the systems and methods described herein are not limited to culture plate images and can be used with any culture media images.

Implementations disclosed herein provide systems, methods and apparatus for consulting on culture plate readings. One skilled in the art will recognize that these embodiments may be implemented in hardware, software, firmware, or any combination thereof.

The functions described herein may be stored as one or more instructions on a processor-readable or computer-readable medium. The term "computer-readable medium" refers to any available medium that can be accessed by a computer or processor. By way of example, and not limitation, such a medium may comprise RAM, ROM, EEPROM, flash memory, CD-ROM or other optical disk storage, magnetic disk storage or other magnetic storage devices, or any other medium that can be used to store desired program code in the form of instructions or data structures and that can be accessed by a computer. Disk and disc, as used herein, includes compact disc (CD), laser disc, optical disc, digital versatile disc (DVD), floppy disk and Blu-ray® disc where disks usually reproduce data magnetically, while discs reproduce data optically with lasers. It should be noted that a computer-readable medium may be tangible and non-transitory. The term "computer-program product" refers to a computing device or processor in combination with code or instructions (e.g., a "program") that may be executed, processed or computed by the computing device or processor. As used herein, the term "code" may refer to software, instructions, code or data that is/are executable by a computing device or processor.

Software or instructions may also be transmitted over a transmission medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of transmission medium.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component or directly connected to the second component. As used herein, the term "plurality" denotes two or more. For example, a plurality of components indicates two or more components.

The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

In the foregoing description, specific details are given to provide a thorough understanding of the examples. However, it will be understood by one of ordinary skill in the art that the examples may be practiced without these specific details. For example, electrical components/devices may be shown in block diagrams in order not to obscure the examples in unnecessary detail. In other instances, such components, other structures and techniques may be shown in detail to further explain the examples.

Headings are included herein for reference and to aid in locating various sections. These headings are not intended to limit the scope of the concepts described with respect thereto. Such concepts may have applicability throughout the entire specification.

It is also noted that the examples may be described as a process, which is depicted as a flowchart, a flow diagram, a finite state diagram, a structure diagram, or a block diagram. Although a flowchart may describe the operations as a sequential process, many of the operations can be performed in parallel, or concurrently, and the process can be repeated. In addition, the order of the operations may be re-arranged. A process is terminated when its operations are completed. A process may correspond to a method, a function, a procedure, a subroutine, a subprogram, etc. When a process corresponds to a software function, its termination corresponds to a return of the function to the calling function or the main function.

The previous description of the disclosed implementations is provided to enable any person skilled in the art to make or use the present invention. Various modifications to these implementations will be readily apparent to those skilled in the art, and the generic principles defined herein may be applied to other implementations without departing from the spirit or scope of the invention. Thus, the present invention is not intended to be limited to the implementations shown herein but is to be accorded the widest scope consistent with the principles and novel features disclosed herein.

What is claimed is:

1. A system for sharing data related to a culture plate image, comprising:
    a first device comprising:
        a user interface configured to display one or more culture plate images and one or more culture plate image annotation tools;
        an input configured to allow a technician to interact with the user interface, wherein the input is configured to allow manipulation of the one or more annotation tools to annotate the one or more culture plate images;
        a communications module configured to transmit data to and receive data from one or more external devices or networks;
        a microphone configured to record an audio communication; and
        a processor configured to:
            process data received from the user interface;
            associate one or more annotations performed using the one or more annotation tools via the input with the one or more culture plate images;
            associate the audio communication with the one or more culture plate images; and
            instruct the communications module to transmit the one or more culture plate images, the audio communication associated with the one or more culture plate images, and the one or more annotations associated with the one or more culture plate images to a second device; and
    the second device, wherein the second device comprises:
        a communications module configured to receive data from the first device, the communications module being configured to receive the one or more culture plate images from the first device;
        a user interface configured to display the one or more culture plate images and one or more annotation tools; and
        an input configured to allow manipulation of the one or more annotation tools of the user interface of the second device to annotate the one or more culture plate images displayed on the user interface of the second device.

2. The system of claim 1, wherein the communications module is configured to receive the one or more culture plate images from an imaging device.

3. The system of claim 1, wherein the first device comprises a camera configured to record a video of the user interface.

4. The system of claim 3, wherein the processor is configured to instruct the communications module to transmit the video to the second device.

5. The system of claim 1, wherein the second device further comprises a processor configured to:
    process data received from the user interface of the second device;
    associate one or more annotations performed using the one or more annotation tools of the user interface of the second device with the one or more culture plate images; and
    instruct the communications module to transmit the one or more culture plate images and one or more annotations performed using the one or more annotations tools of the user interface of the second device associated with the one or more culture plate images to the first device.

6. The system of claim 5, wherein the first device and the second device are configured to communicate via peer-to-peer networking.

7. The system of claim 5, wherein the system is configured to allow simultaneous annotation of the one or more culture plate images using both the first device and the second device.

8. The system of claim 1, wherein the processor is configured to transmit the one or more culture plate images, the audio communication associated with the one or more culture plate images, and the one or more annotations associated with the one or more culture plate images to a computer network, wherein the computer network is configured to store the one or more culture plate images, the audio communication associated with the one or more culture plate images, and the one or more annotations associated with the one or more culture plate images.

9. The system of claim 8, wherein the second device is in communication with the computer network, wherein the second device is configured to retrieve the one or more culture plate images, the audio communication associated with the one or more culture plate images, and the one or more annotations associated with the one or more culture plate images stored by the computer network.

10. The system of claim 9, wherein the computer network is configured to transmit a notification to the second device when the computer network receives the one or more culture plate images, the audio communication associated with the one or more culture plate images, and the one or more annotations associated with the one or more culture plate images from the first device.

11. A method for sharing data related to a culture plate image, the method comprising:
displaying one or more culture plate images and one or more culture plate image annotation tools on a user interface of a first device;
annotating the one or more culture plate images with one or more annotations in response to manipulation of an input of the first device;
recording an audio communication;
associating each of the one or more annotations with the one or more culture plate images by a processor;
associating the audio communication with the one or more culture plate images by the processor;
transmitting the one or more culture plate images, the audio communication associated with the one or more culture plate images, and the one or more annotations associated with the one or more culture plate images to a second device by a communications module;
displaying the one or more culture plate images and the one or more annotations associated with the one or more culture plate images on a user interface of the second device; and
annotating the one or more culture plate images in response to manipulation of an input of the second device.

12. The method of claim 11, further comprising receiving the one or more culture plate images from an imaging device.

13. The method of claim 11, further comprising recording a video of the user interface displaying the one or more culture plate images and the one or more annotations associated with the one or more culture plate images.

14. The method of claim 13, wherein transmitting the one or more culture plate images, the audio communication associated with the one or more culture plate images, and the one or more annotations associated with the one or more culture plate images to the second device comprises transmitting the video to the second device.

15. The method of claim 11, further comprising receiving, by the first device, the one or more culture plate images and one or more annotations performed using one or more annotation tools of the user interface of the second device associated with the one or more culture plate images.

16. The method of claim 15, wherein the first device and the second device are configured to communicate via peer-to-peer networking.

17. The method of claim 15, wherein annotating the one or more culture plate images with one or more annotations in response to manipulation of the input of the first device and annotating the one or more culture plate images in response to manipulation of an input of the second device can be performed simultaneously by the first device and the second device.

18. The method of claim 11, further comprising storing the one or more culture plate images, the audio communication associated with the one or more culture plate images, and the one or more annotations associated with the one or more culture plate images in a memory.

19. The method of claim 18, further comprising transmitting a notification to the second device that the one or more culture plate images, the audio communication associated with the one or more culture plate images, and the one or more annotations associated with the one or more culture plate images are available for retrieval from the memory.

* * * * *